United States Patent [19]

Naito et al.

[11] 3,946,000

[45] *Mar. 23, 1976

[54] 7-[α-(2-AMINOMETHYL-1-CYCLOHEXENYL)-ACETAMIDO]-3-HETEROCYCLIC THIOMETHYL-3-CEPHEM-4-CARBOXYLIC ACIDS

[75] Inventors: Takayuki Naito, Tokyo; Jun Okumura; Hajime Kamachi, both of Yokohama, all of Japan

[73] Assignee: Bristol-Myers Company, New York, N.Y.

[ * ] Notice: The portion of the term of this patent subsequent to Sept. 23, 1992, has been disclaimed.

[22] Filed: Oct. 31, 1973

[21] Appl. No.: 411,559

[52] U.S. Cl............ 260/243 C; 260/240 G; 424/246
[51] Int. Cl.²...................................... C07D 501/20
[58] Field of Search ................................ 260/243 C

[56] References Cited

UNITED STATES PATENTS

| | | | |
|---|---|---|---|
| 3,485,819 | 12/1969 | Weisenborn et al. | 260/243 C |
| 3,673,183 | 6/1972 | Erickson | 260/243 C |
| 3,766,175 | 10/1973 | Lemieux | 260/243 C |
| 3,839,329 | 10/1974 | Brever et al. | 260/243 C |

*Primary Examiner*—Nicholas S. Rizzo
*Attorney, Agent, or Firm*—Herbert W. Taylor, Jr.

[57] ABSTRACT

7-[α-(2-Aminomethyl-1-cyclohexyl)-acetamido]-3-heterocyclic thiomethyl-3-cephem-4-carboxylic acids, and their nontoxic, pharmaceutically acceptable salts and their Schiff bases, as made by reaction of salicylaldehyde with the free amino group, are valuable as antibacterial agents and are particularly valuable as therapeutic agents in poultry and animals, including man, in the treatment of infectious diseases caused by many Gram-positive and Gram-negative bacteria.

51 Claims, No Drawings

7-|α-(2-AMINOMETHYL-1-CYCLOHEXENYL)-ACETAMIDO]-3-HETEROCYCLIC THIOMETHYL-3-CEPHEM-4-CARBOXYLIC ACIDS

BACKGROUND OF THE INVENTION

1. Field of the Invention

The cephalosporins of the present invention possess the usual attributes of such compounds and are particularly useful in the treatment of bacterial infections by parenteral administration.

2. Description of the Prior Art

The cephalosporins are a well-known group of semi-synthetic antibacterial agents made originally, for example, by acylation of the 7-amino group of the nucleus 7-aminocephalosporanic acid (7-ACA) and later by similar acylation of nuclei derived therefrom, as by modification of its substituent at the 3-position. Various reviews have appeared in the scientific literature (e.g. Cephalosporins and Penicllins - Chemistry and Biology, edited by Edwin H. Flynn, Academic Press, New York, 1972, and particularly pages 554–569) and in the patent literature, e.g. as in U.S. Pat. Nos. 3,687,948, 3,741,965, 3,759,904 and 3,759,905 (all U.S. Class 260-243C).

Issued patents on 3-thiolated cephalosporins in which the 7-substituent is a. α-Amino-α-phenylacetamido include U.S. Pat. Nos. 3,641,021, 3,734,907, 3,687,948, 3,741,965, 3,757,015, 3,743,644, Japan 71/24400 (Farmdoc 46374S), Belgium 776,222 (Farmdoc 38983T; U.K. 1,328,340 which includes various substituents on the benzene ring), Belgium 772,592 (Farmdoc 19696T; U.S. Pat. Nos. 3,687,948, 3,734,907 and 3,757,012), West Germany 2,202,274 (Farmdoc 50428T) corresponding to U.S. Pat. No. 3,759,904, Netherlands 7205644 (Farmdoc 76309T; U.S. Pat. No. 3,757,014); and b. o-, m- or p-aminoethoxyphenylacetamido as Netherlands 72/13968 (Farmdoc 24740U) corresponding to U.S. Pat. No. 3,759,905 and c. o-aminomethylphenylacetamido as Netherlands 72/06326 (Farmdoc 76374T) (which also reviews the older patent literature concerning substituted 7-phenylacetamidocephalosporanic acids) corresponding to U.S. Pat. Nos. 3,766,176 and 3,766,175; and d. N-(phenylacetimidoyl)aminoacetamido as U.S. Pat. No. 3,692,779; and e. α-amino-α-(1,4-cyclohexadienyl)acetamido as in Belgium 776,222 (Farmdoc 38983T; U.K. 1,328,340).

Additional similar disclosures are found in U.S. Pat. No. 3,692,779 (Belgium 771,189; Farmdoc 12,819T), Japan 72/05550 (Farmdoc 12,921T), Japan 72/05551 (Farmdoc 12,922T), U.S. Pat. No. 3,719,673 (Belgium 759,570; Farmdoc 39819S), Belgium 793,311 (Farmdoc 39702U) and Belgium 793,191 (Farmdoc 39684U).

Issued patents containing a partially hydrogenated benzene ring in the 7-substituent but lacking a thiomethyl group at the 3-position include those in which the 7-substituent is a. 2-(1,4-cyclohexadien-1-yl)acetamido as in U.S. Pat. No. 3,704,297 (Farmdoc 78154T) and Belgium 759,326 (Farmdoc 38,172S); and b. α-amino-α-(1,4-cyclohexadienyl)acetamido and related compounds as in U.S. Pat. No. 3,485,819; West Germany 2,152,745 (Farmdoc 29606T); and c. α-amino-α-(1,2-cyclohexenyl)acetamido as in Belgium 773,773 (Farmdoc 25515T) and, with a fully unsaturated benzene ring.

d. p-(α-aminoalkyl)phenylacetamido as in U.S. Pat. No. 3,382,241; and e. o-aminomethylphenylthioacetamido as in U.S. Pat. No. 3,657,232.

SUMMARY OF THE INVENTION

This invention comprises the compounds of the formula

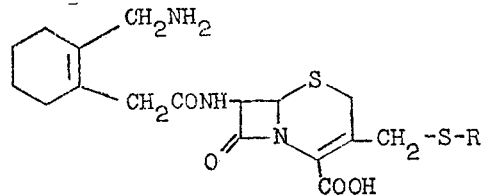

I wherein R is

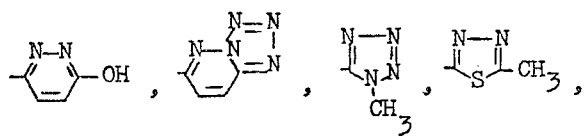

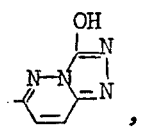

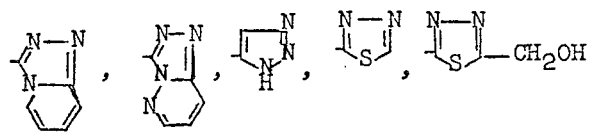

and their nontoxic, pharmaceutically acceptable salts and Schiff bases, as with salicylaldehyde.

In the preferred embodiments of the present invention R is

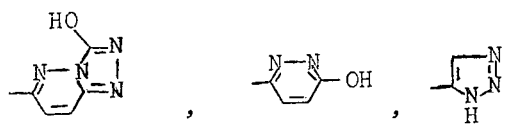, 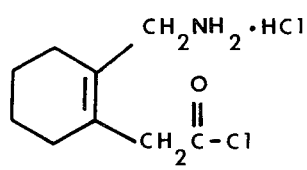

and especially

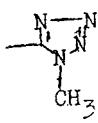

Such salts include carboxylic acid salts including nontoxic metallic salts such as sodium, potassium, calcium and aluminum, the ammonium salt and substituted ammonium salts, e.g. salts of such nontoxic amines as trialkylamines, including triethylamine, procaine, dibenzylamine, N-benzyl-beta-phenethylamine, 1-ephenamine, N,N′-dibenzylethylenediamine, dehydroabietylamine, N,N′-bis-dehydroabietylethylenediamine, N-(lower)-alkylpiperidine, e.g. N-ethylpiperidine, and other amines which have been used to form salts with benzylpenicillin; and in all cases the nontoxic, acid addition salts thereof (i.e., the amine salts) including the mineral acid addition salts such as the hydrochloride, hydrobromide, hydroiodide, sulfate, sulfamate and phosphate and the organic acid addition salts such as the maleate, acetate, citrate, oxalate, succinate, benzoate, tartrate, fumarate, malate, mandelate, ascorbate and the like.

The compounds of the present invention are prepared according to the present invention by coupling with a compound of the formula

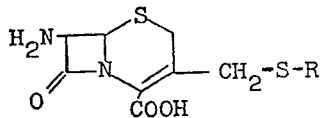 II wherein R has the meaning set out above (or a salt or easily hydrolyzed ester thereof including those of U.S. Pat. 3,284,451 and U.K. 1,229,453 and any of the silyl esters described in U.S. Pat. 3,249,622 for use with 7-aminopenicillanic acid and used in Great Britain 1,073,530) a particular acid or its functional equivalent as an acylating agent for a primary amino group. After coupling, the blocking group is removed to give the desired product. Said acid has the formula

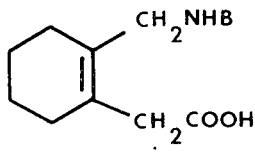

wherein B represents a blocking group of the type used either in peptide syntheses or in any of the numerous syntheses of α-aminobenzylpenicillin from 2-phenylglycine. Particularly valuable blocking groups are a proton, as in the compound of the formula or a β-diketone as in Great Britain 1,123,333, e.g. methyl acetoacetate, in which case the acid containing the blocked amino group is preferably converted to a mixed anhydride, as with ethyl chloroformate, before reaction with compound II or a salt thereof to form the desired product I after acid cleavage.

Further to the discussion above of blocking groups used on the free amino group of the sidechain acid during its coupling with compound II, the blocking group is then removed to form the products of the present invention, e.g., the t-butoxy-carbonyl group is removed by treatment with formic acid, the carbobenzyloxy group is removed by catalytic hydrogenation, the 2-hydroxy-1-naphthcarbonyl group is removed by acid hydrolysis and the trichloroethoxycarbonyl group by treatment with zinc dust in glacial acetic acid. Obviously, other functionally equivalent blocking groups for an amino group can be used and such groups are considered within the scope of this invention.

Thus, with respect to said acid to be used to couple with compound II, functional equivalents include the corresponding acid anhydrides, including mixed anhydrides and particularly the mixed anhydrides prepared from stronger acids such as the lower aliphatic monoesters of carbonic acid, or alkyl and aryl sulfonic acids and of more hindered acids such as diphenylacetic acid. In addition, an acid azide or an active ester of thioester (e.g., with p-nitrophenol, 2,4-dinitrophenol, thiophenol, thioacetic acid) may be used or the free acid itself may be coupled with compound II after first reacting said free acid with N,N′-dimethylchloroforminium chloride [cf. Great Britain, 1,008,170 and Novak and Weichet, Experientia XXI, 6, 360 (1965)] or by the use of enzymes or of an N,N′-carbonyldiimidazole or an N,N′-carbonylditriazole [cf. South African patent specification 63/2684] or a carbodiimide reagent [especially N,N′-dicyclohexylcarbodiimide, N,N′-diisopropylcarbodiimide or N-cyclohexyl-N′-(2-morpholinoethyl)carbodiimide; cf. Sheehan and Hess, J. Amer. Chem. Soc., 77, 1067 (1955)] or of alkylamine reagent [cf. R. Buijle and H. G. Viehe, Angew Chem. International Edition 3, 582 (1964)], or of a ketenimine reagent [cf. C. L. Stevens and M. E. Mond, J. Amer. Chem. Soc., 80, (4065)] or of an isoxazolium salt reagent [cf. R. B. Woodward, R. A. Olofson and H. Mayer, J. Amer. Chem. Soc. 83, 1010 (1961)]. Another equivalent of the acid chloride is a corresponding azolide, i.e., an amide of the corresponding acid whose amide nitrogen is a member of an quasiaromatic five-membered ring containing at least two nitrogen atoms, i.e., imidazole, pyrazole, the triazoles, benzimidazole, benzotriazole and their substituted derivatives. As an example of the general method for the preparation of an azolide, N,N′-carbonyldiimidazole is reacted with a carboxylic acid in equimolar proportions at room temperature in tetrahydrofuran, chloroform, dimethylformamide or a similar inert solvent to form the carboxylic acid imidazolide in practically quantitative yield with liberation of carbon dioxide and one mole of imidazole. Dicarboxylic acids yield dimidazolide. The byproduct, imidazole, precipitates and may be separated and the imidazolide isolated, but this is not essential. The methods for carrying out these reactions to produce a cephalosporin and the methods used to isolate the cephalosporin so produced are well known in the art.

In the treatment of bacterial infections in man, the compounds of this invention are administered parenterally, in accordance with conventional procedures for antibiotic administration, in an amount of from about 5 to 200 mg./kg./day and preferably about 5 to 20 mg./kg./day in divided dosage, e.g., three to four times a day. They are administered in dosage units containing, for example, 125 or 250 or 500 mg. of active ingredient with suitable physiologically acceptable carriers or excipients. The dosage units are in the form of liquid preparations such as solutions or suspensions.

Certain 3-substituted 7-[α-(2-aminomethylphenyl)acetamido]cephalosporanic acid derivatives (A; see Netherlands 72/06326, Farmdoc 76374T, corresponding to U.S. Ser. No. 142,337 filed May 11, 1971) provide a series of parenteral-use cephalosporins which are very effective derivatives with a broad spectrum of activity. Their limited water solubility (<2 mg./ml.) has, however, caused crystalluria formation even when the antibiotics had been administered parenterally as a readily-dissociable soluble derivative. The object of the present invention was, therefore, to obtain equally active compounds which show higher water solubility as the zwitterion form.

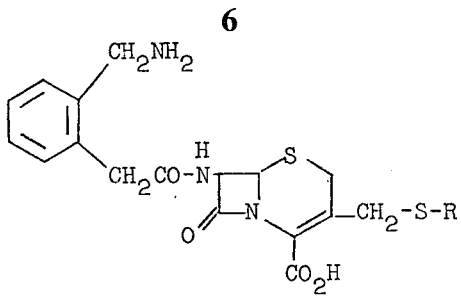

(A)

There is provided by the present invention certain 7-[α-(2-aminomethyl-1-cyclohexenyl)acetamido]-cephalosporanic acids (B).

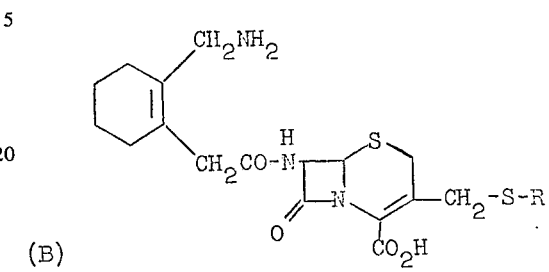

(B)

Many of the new series were found to be more soluble than the corresponding phenyl derivatives and to have a solubility of more than 7 mg./ml. determined routinely in 0.1 M pH 7.0 phosphate buffer, as shown below compared with that of certain corresponding phenyl derivatives.

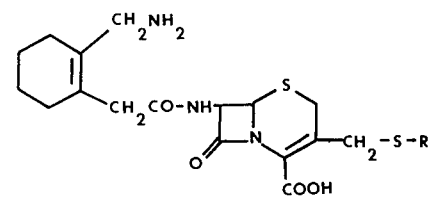

(B)

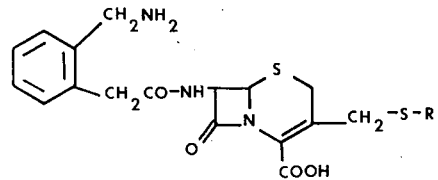

(A)

| R= | | Solubility* | Solubility* | |
|---|---|---|---|---|
| ![N-N OH] | Ex. 1 | 16.0–16.8 mg./ml. | 4.4 mg./ml. | (1) |
| ![tetrazole] | Ex. 2 | 3.0 mg./ml. | 3.5 mg./ml. | (2) |
| ![N-methyltetrazole] | Ex. 3 | 23–26 mg./ml. | 1.9 mg./ml. | (3) |
| ![methylthiadiazole] | Ex. 4 | 4.3–4.6 mg./ml. | 0.9 mg./ml. | (4) |

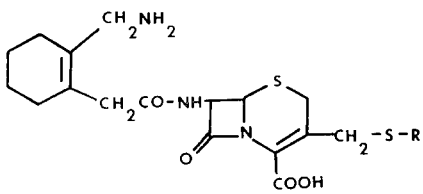

(B)

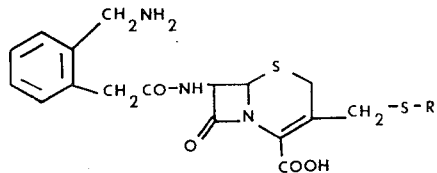

(A)

| R= | | Solubility* | Solubility* |
|---|---|---|---|
| 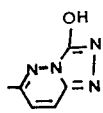 | Ex. 5 | 8 mg./ml. | 3.6 mg./ml. |

*Stirred at 25° C. for 4 hours in 0.1 M pH 7.0 phosphate buffer—filtered through Milipore filter (0.45 μ)—assayed spectroscopically against its own standard.
(1) This compound (also called BB-S150) is claimed in U.S.S.N. 285,764 filed August 31, 1972 and issued May 28, 1974 as U.S. 3,813,376.
(2) This compound (also called BB-S226) is claimed in U.S.S.N. 284,792 filed August 30, 1972 and issued June 4, 1974 as U.S. 3,814,755.
(3) This compound (also called MR-S94) is claimed in U.S.S.N. 142,337 filed May 11, 1971 (see Netherlands 72/06326; Farmdoc 76,374T) and issued October 16, 1973 as U.S. 3,766,175.
(4) This compound (also called MR-S96) is claimed in U.S.S.N. 142,337 filed May 11, 1971 (see Netherlands 72/06326; Farmdoc 76,374T) and issued October 16, 1973 as U.S. 3,766,175.

Preparation of
7-[α-(2-Aminomethyl-1-cyclohexenyl)acetamido]-
cephalosporanic acid derivatives

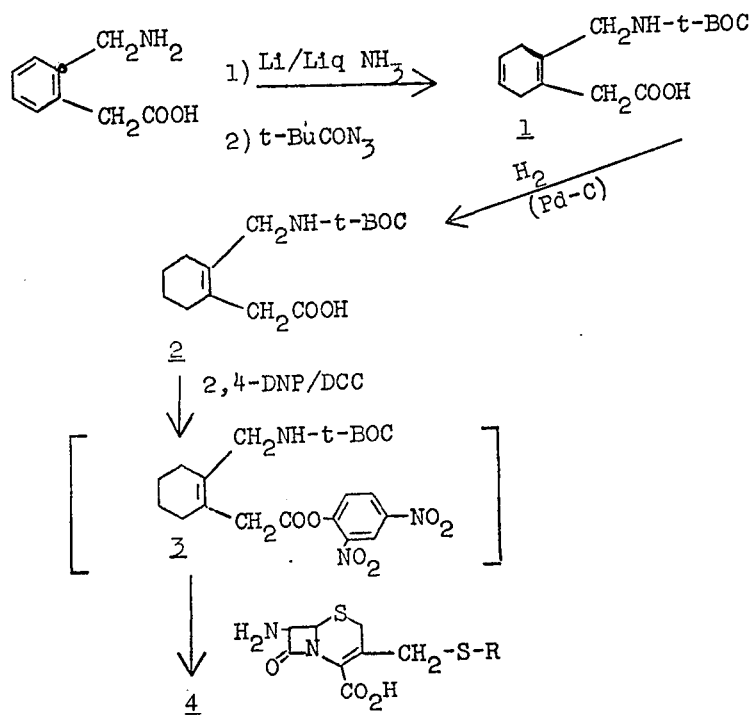

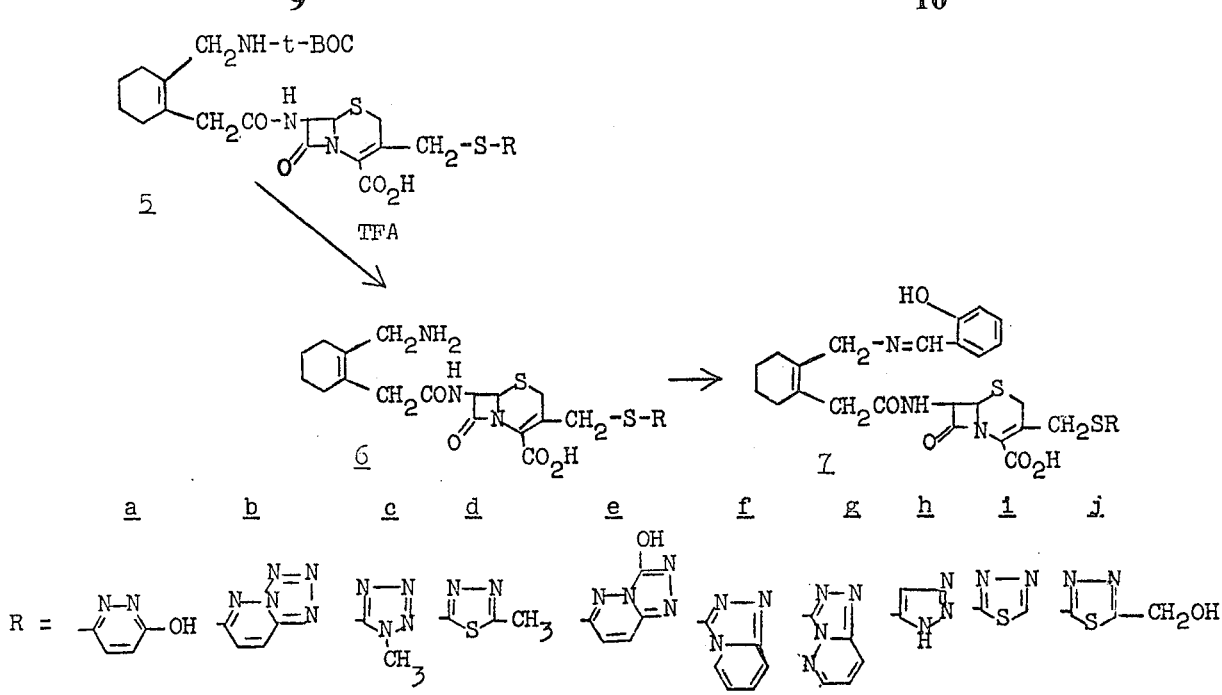

The following examples are given in illustration of, but not in limitation of, the present invention. All temperatures are given in degrees Centigrade. "Skellysolve B" is a petroleum ether fraction of B.P. 60°–68° C. consisting essentially of n-hexane. IR-120 is also called Amberlite IR-120 and is a strong cation exchange resin containing sulfonic acid radicals. Amberlite IR-120 is a commercially available cation exchange resin of the polystyrene sulfonic acid type; it is thus a nuclear sulfonated polystyrene resin cross-linked with divinyl benzene obtained by the procedure given by Kunin, Ion Exchange Resins, 2nd. Edition (1958), John Wiley and Sons, Inc. Therein see pages 84 and 87 for example.

2,4-Dinitrophenol is represented as 2,4-DNP, N,N'-dicyclohexylcarbodiimide as DCC, trifuloroacetic acid as TFA, tetrahydrofuran as THF, t-butoxycarbonyl azide as t-BuCON$_3$ and t-butoxycarbonyl as t-BOC.

Preparation of Starting Materials

α-(2-Aminomethyl-1,4-cyclohexadienyl)acetic acid

A solution of 16.5 g. (0.1 mole) of o-aminomethylphenylacetic acid in 1.5 l of liquid ammonia (which had been treated with 50 mg. of Li to remove a trace of moisture) was slowly diluted with 500 ml. of dry t-BuOH. To the solution was added in small portions 3.4 g. (0.5 atom) of Li over a period of 4 hours and the mixture was stirred for 16 hours at room temperature removing the liquid ammonia in a hood and finally evaporated to dryness below 40° C. The residue was dissolved in 500 ml. of water and the solution was chromatographed on a column of IR-120 (H$^+$,700 ml.) resin and eluted with 1% NH$_4$OH solution. Ninhydrin positive fractions of the eluate were combined and evaporated to dryness. The residue was washed with four 50 ml. portions of hot acetone and recrystallized from 500 ml. of ethanol-water (1:1) to give 11.2 g. (67%) of α-(2-aminomethyl-1,4-cyclohexadienyl)acetic acid as colorless needles. M.p. 183°C.

IR: $\nu_{max}^{nuj}$ 1630, 1520, 1380, 1356 cm$^{-1}$.
NMR: $\delta_{D_2O + K_2CO_3}$ 2.72 (4H, s, $\underline{H}_2$C<=), 3.01 (2H, s, CH$_2$CO), 3.20 (2H, s, C$\underline{H}_2$—N), 5.78 (2H, s, $\underline{H}$>C=).

Anal. Calcd. for C$_9$H$_{13}$NO$_2$: C, 64.65; H, 7.84; N, 8.38. Found: C, 64.77; H, 8.06; N, 8.44.

Alternative Procedure for the Preparation of α-(2-aminomethyl-1,4-cyclohexadienyl)-acetic acid

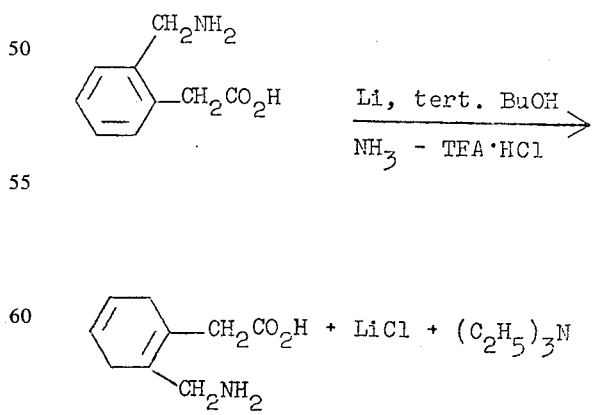

The procedure used by Welch, Dolfini and Giarrusso in U.S. Pat. 3,720,665 (Example 1) to make D-2-amino-2-(1,4-cyclohexadienyl)acetic acid was adapted. A solution of 830 ml. of distilled liquid ammonia was dried with 40 mg. of lithium under an argon atmosphere. To this stirred solution was added 11.0 g. (0.07 mole) of 2-aminomethylphenylacetic acid and 340 ml. of tert. butyl alcohol. A total of 1.6 g. (0.225 mole) of lithium was added to the vigorously stirred solution over a period of 2 hours. The grey mixture was then treated with 35 g. (0.215 mole) of triethylamine (TEA) hydrochloride and stirred overnight at room temperature for 18 hours. The tert. butyl alcohol was removed at 40° (15 mm.) to yield a white residue which was dried in vacuo over $P_2O_5$ overnight. The solid was dissolved in 30 ml. of 1:1 methanol-water and added with stirring to 3.5 l. of 1:1 chloroform-acetone at 5°. the mixture was stirred for 20 min. and the amino acid α-(2-aminomethyl-1,4-cyclohexadienyl)acetic acid, was collected and dried for 16 hours in vacuo over $P_2O_5$ to yield 6.3 g. (58%) of white crystals, m.p. 190° decomp. The IR and NMR spectra were consistent for the structure.

α-[2-(t-Butoxycarbonylaminomethyl)-1,4-cyclohexadienyl]acetic acid (1)

To a stirred solution of 8.0 g. (0.048 mole) of α-(2-aminomethyl-1,4-cyclohexadienyl)acetic acid and 3.8 g. (0.096 mole) of NaOH in 150 ml. of water was added a solution of 10.3 g. (0.072 mole) of t-butoxycarbonylazide in 80 ml. of THF and the mixture was stirred for 18 hours at room temperature. The THF was removed under reduced pressure and the residual solution was washed with ether (2 × 100 ml.), acidified with 6 N HCl and extracted with ether (3 × 100 ml.). The combined extracts were washed with water (2 × 100 ml.) and a saturated NaCl solution (100 ml.), dried with $Na_2SO_4$ and evaporated to dryness. The oily residue was triturated with n-hexane to give 10.5 g. (82%) of colorless powder 1 melting at 113° C.

IR: $\nu_{max}^{nuj}$ 3370, 1715, 1640, 1530, 1280, 1160 cm$^{-1}$.

NMR: $\delta_{ppm}^{CDCl_3}$ 1.45 (9H, s, t-Bu-H), 2.73 (4H, s, $H_2C<^{C=C}$), 3.16 (2H, s, $CH_2CO$); 3.76 (2H, d, 6Hz, $CH_2N$) 4.90 (1H, m, N$\underline{H}$), 5.66 (2H, s, $\underline{H}$>C=), 10.6 (1H, br-s, COO$\underline{H}$).

Anal. Calcd. for $C_{14}H_{21}NO_4$: C, 62.90; H, 7.92; N, 5.24. Found: C, 63.13; H, 8.21; N, 5.26.

[2-N(N-t-Butoxycarbonylamino)methyl-1-cyclohexen-1-yl]acetic acid (2)

A solution of [2-(N-t-butoxycarbonylamino)methyl-1,4-cyclohexadien-1-yl]acetic acid (1), (1.33 g., 5 mmoles) in 3% ammonium hydroxide (10 ml.) was hydrogenated at 40 psi with palladium on charcoal (10%, 0.2 g.). A theoretical amount of hydrogen was taken up in 3 hours. The catalyst was removed and the filtrate was acidified to pH 2 with dil. HCl and extracted with ethyl acetate (2 × 50 ml.). The combined extracts were washed with water (20 ml.), dried with $Na_2SO_4$ and evaporated under reduced pressure to afford an oil (1.34 g.) which solidified on standing for several days. Recyrstallization from n-hexane - ethyl acetate gave 1.2 g. (90%) of 2 as colorless prisms melting at 118°-119° C.

IR: $\nu_{max}^{nujol}$ 3450, 1730, 1660, 1510 cm$^{-1}$.

NMR: $\delta_{ppm}^{CDCl_3}$ 1.58 (9H, s, t-butyl-$\underline{H}$), 1.50 – 1.90 (4H, m, —$CH_2$—), 1.90 – 2.20 (4H, m, allylic methylene-$\underline{H}$), 3.18 (2H, s, $CH_2$—CO), 3.78 (2H, d, 6 Hz, $CH_2$ —N), 5.00 (1H, br-s, NH), 8.98 (1H, br-s, COOH).

Anal. Calcd. for $C_{14}H_{23}NO_4$: C, 62.43; H, 8.61; N, 5.20. Found: C, 62.12; H, 8.77; N, 5.37.

7-Amino-3-(3-hydroxypyridazin-6-ylthiomethyl)-3-cephem-4-carboxylic acid (4a)

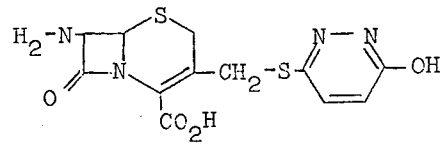

3-Chloro-6-hydroxypyridazine

A mixture of 22.47 g. (0.15 mole) of 3,6-dichloropyridazine and 50 ml. of acetic acid was refluxed for two hours. The reaction mixture was cooled and diluted with 50 ml. of water and then concentrated to dryness under reduced pressure. The residue was crystallized from water to give 15.8 g. (80%) of 3-chloro-6-hydroxypyridazine as colorless prisms which melted at 133°-7° C. (lit. 138°-140° C.). See N. Takabayashi, Yakugaku Zasshi, 75, 778 (1955).

3-Hydroxy-6-mercaptopyridazine

A mixture of 2.6 g. (0.02 mole) of 3-chloro-6-hydroxypyridazine and 5.0 g. (0.07 mole) of freshly prepared potassium hydrogen sulfide in 30 ml. of ethanol was heated at 130°–140° C. in a sealed tube for 6 hours. The reaction mixture was cooled and diluted with 200 ml. of water. Almost all organic solvent was removed by distillation under reduced pressure. The residual aqueous solution was acidified with dilute hydrochloric acid to pH 3 and extracted with ethyl acetate (6 × 50 ml.). The combined extracts were evaporated to dryness and the residue was reprecipitated from 30 ml. of ethanol-ligroin (1:1) to give 2.2 g. (87%) of amorphous 3-hydroxy-6-mercaptopyridazine. m.p. 158° – 159° C. (lit. 157°–158° C.

See J. Druey et al., Helv. Chem. Acta. 37, 121 (1954).

3-Hydroxy-6-mercaptopyridazine

To a solution of 5.6 g. (0.05 mole) of 3,6-dihydroxypyridazine in 150 ml. of pyridine was added portionwise 2.70 g. (0.012 mole) of phosphorus pentasulfide with vigorous stirring under refluxing. The refluxing was continued for one hour and then the reaction mixture was diluted with 200 ml. of water and concentrated to remove the pyridine. The resulting oily residue was suspended in water and extracted with ethyl acetate. The organic extracts were combined and concentrated again to give oily material which was triturated with a small amount of water to give 3-hydroxy-6-mercaptopyridazine as a yellow solid. Recrystallization from water afforded 0.62 g. (12%) of the product which was identical with that prepared above.

3,6-Dihydroxypyridazine

To a boiling solution of 315 g. (3 moles) of hydrazine dihydrochloride in 2 L of water was added portionwise 295 g. (3 moles) of finely ground maleic anhydride with stirring. After the addition was completed the heating was continued for 4 hours and then allowed to stand overnight in a refrigerator to give 285 g. (85%) of 3,6-dihydroxypyridazine as massive pillars. m.p. >290° C.

3,6-Dichloropyridazine

A mixture of 150 g. (1.33 moles) of 3,6-dihydroxypyridazine and 250 g. of phosphorus oxychloride was refluxed for 3 hours under protection from moisture. The excess of phosphorus oxychloride was removed under reduced pressure and the dark residue was poured into one Kg. of crushed ice. The resulting precipitate was collected by filtration. The second crop of the product was obtained from the mother liquor by extraction with five 300 ml. portions of chloroform followed by treating with 1g. of charcoal and evaporating the solvent. The first and second crops were combined, dissolved in 500 ml. of chloroform and treated again with one g. of charcoal and concentrated to give 165 g. (83%) of 3,6-dichloropyridazine as fine needles melting at 60°–61° C. (in a sealed tube).

6-Chloro-3-hydroxypyridazine

A suspension of 60 g. (0.4 mole) of 3,6-dichloropyridazine in 200 ml. of 10% hydrochloric acid was refluxed for 2 hours until a clear solution was obtained. The clear solution was treated with ca. 1.5 g. of active carbon and filtered. The filtrate was concentrated under reduced pressure to give 6-chloro-3-hydroxypyridazine as colorless needles. Yield 49.5 g. (98%). M.p. 137°–139° C.

3-Hydroxy-6-mercaptopyridazine

A mixture of 50 g. (0.38 mole) of 6-chloro-3-hydroxypyridazine, 60 g. (0.83 mole) of potassium hydrogen sulfide in 250 ml. of ethanol was heated in a 500 ml. autoclave at 140°C. for 14 hours with magnetic stirring. The pressure reached to 15–20 Kg./cm$^2$. The mixture was evaporated to dryness and the residue was dissolved in 300 ml. of water. The aqueous solution was acidified with dil. hydrochloric acid to pH 3 and extracted with ten 200 ml. portions of ethyl acetate. The combined extracts were concentrated to give 34.3 g. (70%) of amorphous 3-hydroxy-6mercaptopyridazine. M.p. 151°–152° C.

7-Amino-3-(6-hydroxypyridazin-3-ylthiomethyl)-3-cephem-4-carboxylic acid

A mixture of 0.60 g. (0.0047 mole) of 3-hydroxy-6-mercaptopyridazine, 1.27 g. (0.0047 mole) of 7-aminocephalosporanic acid, 0.78 g. (0.0094 mole) of sodium bicarbonate in 25 ml. of 0.1 M phosphate buffer (pH 6.4) was heated at 60° C. for 5 hours. The reaction mixture was filtered to remove a trace of insoluble material and the filtrate was adjusted to pH 5 with acetic acid to give brown precipitates, which were collected by filtration, washed with water and acetone successively and dried in vacuo to give 7-amino-3-(6-hydroxypyridazin-3-ylthiomethyl)-3-cephem-4-carboxylic acid; 1.03 g. (71%). M.p. 290°–300° C. (decomp.).

IR: $\nu_{max}^{KBr}$ 1805, 1680, 1650, 1580, 1415 cm$^{-1}$.
UV: $\lambda_{max}^{1\% \ NaOH}$ 249 nm ($\epsilon$ 19400). NMR: $\delta_{ppm}^{D_2O-K_2CO_3}$ 3.22 (1H, d, 19Hz), 3.37 (1H, d, 14 Hz), 3.65 (1H, d, 14 Hz), 3.72 (1H, d, 19 Hz), 4.90 (1H, d, 4 Hz), 5.30 (1H, d, 4Hz), 6.75 (1H, d, 10 Hz), 7.30 (1H, d, 10 Hz).

Anal. Calcd. for $C_{12}H_{12}N_4O_4S_2 \cdot 1/2H_2O$: C, 41.25; H, 3.75; N, 16.04; S, 18.36. Found: C, 41.45; H, 3.70; N, 15.83; S, 18.03.

7-Amino-3-(3-hydroxypyridazine-6-ylthiomethyl)-3-cephem-4-carboxylic acid.

A mixture of 141 g. (0.52 moles) of 7-ACA, 92 g. (1.1 moles) of sodium bicarbonate and 73 g. (0.57 moles) of 3-hydroxy-6-mercaptopyridazine in 1.5 L of 0.1 M phosphate buffer (pH 6.4) was heated at 60°–65° C. under nitrogen atmosphere for 4 hours. The hot mixture was treated with 2 g. of charcoal and filtered. The filtrate was cooled to room temperature and adjusted to pH 4.5 with glacial acetic acid to give the precipitate, which was collected by filtration, washed with one L of acetone and air-dried at room temperature to yield 125 g. (70%) of 7-amino-3-(3-hydroxypyridazine-6-ylthiomethyl)-3-cephem-4-carboxylic acid. M.p. 240°–250° C. (dec.).

7-Amino-3-(tetrazolo[1,5-b]1,5-b]pyridazin-6-ylthiomethyl-3-cephem-4-carboxylic acid (4b)

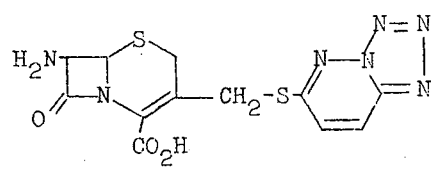

Preparation of 6-Mercaptotetrazolo[4,5-b]pyridazine

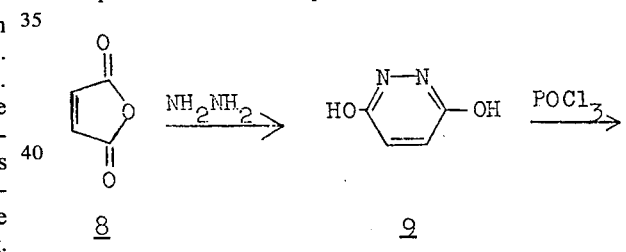

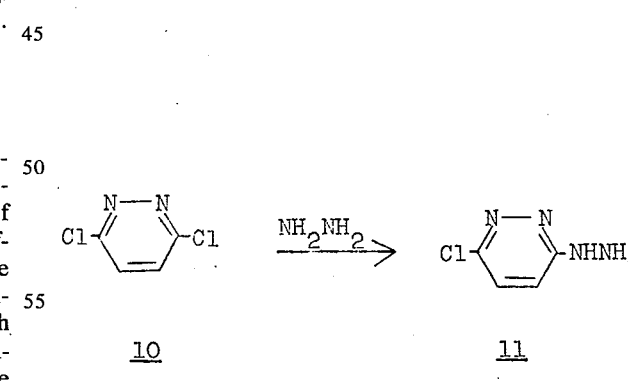

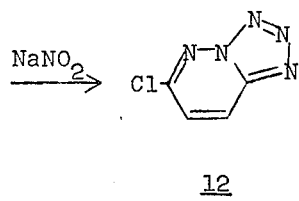

alc. KSH ⟶ 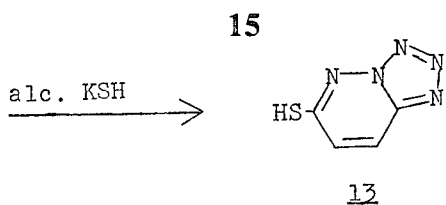

13

3,6-Dihydroxypyridazine (9)

To a boiling solution of 315 g. (3 moles) of hydrazine dihydrochloride in 2 L of water was added portionwise 295 g. (3 moles) of finely ground maleic anhydride with stirring. After the addition was completed the heating was continued for 4 hours and then allowed to stand overnight in a refrigerator to give 285 g. (85%) of 9 massive pillars. m.p. > 290° C.

3,6-Dichloropyridazine (10)

A mixture of 150 g. (1.33 moles) of 9 and 250 g. of phosphorus oxychloride was refluxed for 3 hours under protection from moisture. The excess of phosphorus oxychloride was removed under reduced pressure and the dark residue was poured into one Kg. of crushed ice. The resulting precipitate was collected by filtration. The second crop of the product was obtained from the mother liquor by the extraction with five 300 ml. portions of chloroform followed by treating with 1 g. of charcoal and evaporating the solvent. The first and second crops were combined, dissolved in 500 ml. of chloroform and treated again with one g. of charcoal and concentrated to give 165 g. (83%) of 10 as fine needles melting at 60°–61° C. (in a sealed tube).

3-Chloro-6-hydrazinopyridazine (11)

A mixture of 40 g. (0.27 mole) of 3,6-dichloropyridazine (10) and 40 ml. of 80% hydrazine hydrate in 80 ml. of ethanol was refluxed for one hour. The reaction mixture was evaporated to dryness and the residue was recrystallized from benzene to give 39 g. (100%) of 11 melting at 114°–115° C.

6-Chlorotetrazolo[4,5-b]pyridazine (12)

To a solution of 25.7 g. (0.174 mole) of 11 in 100 ml. of 15% acetic acid was added dropwise a solution of 13.8 g. (0.2 mole) of sodium nitrite in 50 ml. of water with vigorous stirring at 5°–10° C. Stirring was continued for one hour at the same temperature. The precipitate which separated was filtered, washed with 20 ml. of water and air-dried to give 17.02 g. of 12. Additional product was obtained by evaporation of the filtrate. Total yield 18.32 g. (64%). M.p. 104°–105° C.

6-Mercaptotetrazolo[4,5-b]pyridazine (13)

A mixture of 21.3 g. (0.137 mole) of 12 and 20 g. (0.25 mole) of potassium hydrosulfide in 200 ml. of ethanol was refluxed for 2 hours and evaporated to dryness. The residue was dissolved in 100 ml. of water and filtered to remove a small amount of insoluble material. The filtrate was acidified to pH 1 with dil. hydrochloric acid to precipitate 13 as colorless needles which were collected by filtration, washed with 20 ml. of water and dried. Yield 9.80 g. (47%). M.p. 140°–141° C. (dec.).

IR: $\nu_{max}^{KBr}$ 2500, 1540, 1445, 1295, 840 cm$^{-1}$.
NMR: $\sigma_{ppm}^{D_2O+K_2CO_3}$ 7.44 (1H, d, 10 Hz, pyridazine-$\underline{H}$), 7.77 (1H, d, 10 Hz, pyridazine-$\underline{H}$).

Anal. Calcd. for $C_4H_3N_5S$: C, 31.37; H, 1.97; N, 45.72; S, 20.94. Found: C, 31.52; 31.66; H, 1.70, 1.69; N, 46.01; 46.01; S, 20.95.

Preparation of 7-amino-3-(tetrazolo[4,5-b]pyridazin-6-ylthiomethyl)-3-cephem-4-carboxylic acid

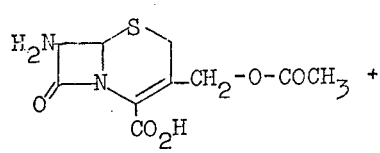

7-ACA

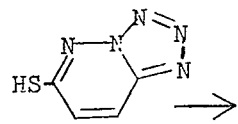

13 ⟶

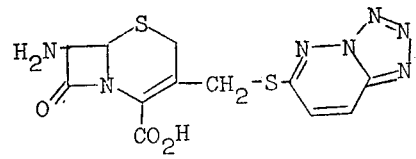

4b

7-Amino-3-(tetrazolo[4,5-b]pyridazin-6-ylthiomethyl)-3-cephem-4-carboxylic acid (4b)

i. To a hot solution (50°–60° C.) of 9.56 g. (0.062 mole) of 13 and 10.42 g. (0.124 mole) of sodium bicarbonate in 300 ml. of water was added carefully 16.86 g. (0.062 mole) of 7-ACA and the mixture was heated at 80°–85° C. for 30 minutes. About 7 g. of sodium bicarbonate was added to the reaction mixture to dissolve insoluble material. The solution was treated with active carbon, filtered and the filtrate was acidified to pH 5 with dil. hydrochloric acid. The precipitate was collected by filtration, washed with water, air-dried and finally in vacuo on $P_2O_5$ to give 14.47 g. (64%) of 4b. M.p. 248°–250° C. (dec.).

ii. A stirred solution of 16.8 g. (0.11 mole) of 13 and 18.48 g. (0.22 mole) of $NaHCO_3$ in 1 L of 0.1 M phosphate buffer (pH 6.4) was heated at 50° C. and to the solution was added portionwise 30 g. (0.11 mole) of 7ACA. The mixture was heated at 80° C. for 2.5 hours, during which period insoluble material still remained. The reaction mixture was cooled to room temperature and the precipitated 4b was collected by filtration, washed thoroughly with 200 ml. of water and air-dried.

Additional 4b was obtained from the filtrate and the washings by acidifying to pH 5 with dil. HCl. Total yield 32.9 g. (83%). M.p. 245°–250° C. (dec.).

IR: $\nu\ _{max}^{KBr}$ 1800, 1615, 1538, 1360 cm$^{-1}$.

UV: $\lambda\ _{max}^{1\%NaHCO_3}$ 237 nm ($\epsilon$ 19500), 275 nm ($\epsilon$ 12000), 310 nm (sh) ($\epsilon$ 5700).

NMR: $\delta\ _{ppm}^{D_2O+K_2CO_3}$ 3.35 (1H, d, 18 Hz, 2-$\underline{H}$), 3.76 (1H, d, 18 Hz, 2-$\underline{H}$), 4.00 (1H, d, 10 Hz, 3-$\underline{CH_2}$), 4.48 (1H, d, 10 Hz, 3-$\underline{CH_2}$), 4.93 (1H, d, 4 Hz, 6-$\underline{H}$), 5.32 (1H, d, 4 Hz, 7-$\underline{H}$), 7.46 (1 H, d, 10 Hz, pyridazine-$\underline{H}$), 8.18 (1H, d, 10 Hz, pyridazine-$\underline{H}$).

Anal. Calcd. for $C_{12}H_{11}N_7O_3S_2$: C, 39.44; H, 3.03; N, 26.83; S, 17.55. Found: C, 39.19; H, 2.71; N, 26.84; S, 17.35.

7-Amino-3-(5-methyl-1,3,4-thiadiazol-2-ylthiomethyl)-3-cephem-4-carboxylic acid (4d)

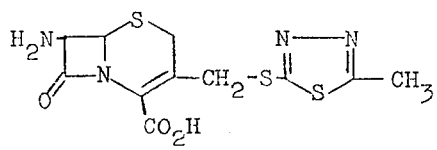

2-Mercapto-5-methyl-1,3,4-thiadiazole.

Lit. ref. U.S. Pat. 3,516,997 (1970); *J. Antibiotics*, 23, 131–36 (1970).

11.5 g. (0.1 mole) of 2-amino-5-methyl-1,3,4-thiadiazole was carefully ground together with 32 g. (0.45 mole) of sodium nitrite and slowly added to 160 ml. of 48% HBr containing 50 mg. of powdered copper at −10° C. with stirring. After the addition was completed, the solution was stirred at −5° C. for one hour and then at 20° C. for one and a half hours. The pH was adjusted to 9.5 by addition of 50% KOH and the solution was heated to 60° C. At 60° C. the pH was readjusted to 9.5 by addition of 50% KOH. The solution was cooled and filtered. The precipitate was dissolved in ether and the filtrate was extracted with 2 × 200 ml. ether. The combined ether solutions were dried over sodium sulfate and evaporated to dryness. The product was recrystallized from benzene-"Skellysolve B". Yield 12 g., m.p. 105°–107° C.

12 g. (.07 mole) of 2-bromo-5-methyl-1,3,4-thiadiazol and 5 g. (0.07 mole) of thiourea were dissolved in 40 ml. of 100% ethanol and refluxed for one and a half hours on a steam bath. This solution was added to 4.5 g. (.08 mole) of KOH in 65 ml. $H_2O$ and the mixture heated to boiling for five minutes. The ethanol was removed under vacuum and the pH of the aqueous solution adjusted to 3 by addition of 3 N HCl. The product crystallized out and after cooling at 0° C. for one hour was collected by filtration, washed with cold water and recrystallized from 100% ethanol. Yield 5 g., m.p. 186°–187° C.

Anal. Calcd. for $C_3H_4N_2S_2$: C, 27.25; H, 3.05; N, 21.19; S, 48.51. Found: C, 27.20; H, 3.34; N, 21.18; S, 48.48.

7-Amino-3-(5-methyl-1,3,4-thiadiazol-2-ylthiomethyl)-3-cephem-4-carboxylic acid.

To a stirred suspension of 2.72 g. (0.01 mole) of 7-ACA in 50 ml. of 0.1 M, pH 6.4 phosphate buffer, was added 1.68 g. (0.02 mole) of $NaHCO_3$ followed by 1.45 g. (0.011 mole) of 2-mercapto-5-methyl-1,3,4-thiadiazole and the mixture heated and stirred at 60° C. for five hours. The resulting slurry was then allowed to cool to about 22° C. over a one hour period. The crystalline precipitate was collected by filtration, washed with water and air dried. Yield 1.3 g., dec. pt. 206° C. Scaling up the reaction 10X gave 18.0 g.

Anal. Calcd. for $C_{11}H_{12}N_4O_3S_3$: C, 38.37; H, 3.52; S, 27.96. Found: C, 39.06; H, 3.91; S, 26.67.

7-Amino-3-(1-methyltetrazol-5-ylthiomethyl)-3-cephem-4-carboxylic acid (4c)

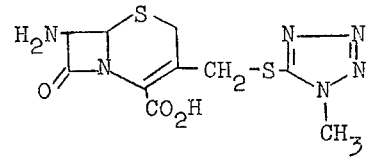

The above preparation was repeated using 1-methyl-1,2,3,4-tetrazole-5-thiol instead of the thiadiazole. There was obtained 25 g. (76%) of 7-amino-3-(1-methyl-1,2,3,4-tetrazole-5-thiomethyl)-$\Delta^3$-cephem-4-carboxylic acid. The preparation of this same compound is also described in U.S. Pat. 3,516,997 in column 6 under the heading "Preparation 7".

7-Amino-3-(3-hydroxypyridazino[3,2-c]-s-triazol-6-ylthiomethyl)-3-cephem-4-carboxylic acid (4e).

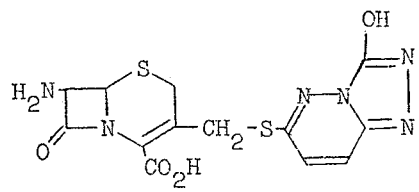

6-Mercapto-2,3-dihydro-s-triazolo[4,3-b]-pyridazin-3-one

A mixture of 6-chloro-2,3-dihydro-s-triazolo[4,3-b]-pyridazin-3-one [P. Francavilla and F. Lauria, J. Het.

Chem., 8, 415 (1971) ] (1.70 g., 0.01 mole) and potassium hydrosulfide (1.44 g., 0.02 mole) in ethanol (30 ml.) was heated in a sealed tube for 8 hours at 140°. After cooling, water (50 ml.) was added to the reaction mixture and a small amount of insoluble material was removed by filtration. The filtrate being concentrated under reduced pressure, the concentrate was acidified to pH 2 with dil. HCl to afford yellow precipitate of 6-mercapto-2,3-dihydro-s-triazolo[4,3-b]pyridazin-3-one which was collected by filtration, washed with water (10 ml.) and dried in vacuo on $P_2O_5$. Yield 1.43 g. (84%). M.p. > 300° C.

IR: $\nu_{max}^{KBr}$ 2500, 1710, 1495, 1350 cm$^{-1}$.

UV: $\lambda_{max}^{1\%NaHCO_3}$ 261 nm ($\epsilon$ 9000), 320 nm ($\epsilon$ 2700)

NMR: $\sigma_{ppm}^{D_2O-K_2CO_3}$ 6.96 (1 H, d, 10 Hz, 7-H or 8-H). 7.12 (1 H, d, 10 Hz, 7-H or 8-H).

Anal. Calcd. for $C_5H_4N_4OS$: C, 35.71; H, 2.40; N, 33.31; S, 19.07. Found: C, 35.17; H, 2.28; N, 33.38; S, 19.76

7-Amino-3-[2,3-dihydro-s-triazolo[4,3-b]pyridazin-3-one-6-ylthiomethyl]-3-cephem-4-carboxylic acid (4e)

7-ACA (1.36 g., 5 mmoles) was added at 50° C. to a solution of 6-mercapto-2,3-dihydro-s-triazolo[4,3-b]pyridazin-3-one (0.84 g., 5 mmoles) and sodium bicarbonate (0.84 g., 10 mmoles) in 20 ml. of 0.1 M phosphate buffer solution (pH 6.4) and the mixture was heated for 2 hours at 70° C. A small amount of insoluble material was removed by filtration and acidification of the filtrate to pH 5 with dil. HCl afforded the product 4e which was collected by filtration, washed with water (30 ml.) and dried in vacuo on $P_2O_5$. Yield of 7-amino-3-[2,3-dihydro-3-triazolo(4,3-b)pyridazin-3-one-6-ylthiomethyl]-3-cephem-4-carboxylic acid 1.25 g. (66%), M.p. > 300° C.

IR: $\nu_{max}^{KBr}$ 1805, 1720, 1620, 1550 cm$^{-1}$.

UV $\lambda_{max}^{1\%NaHCO_3}$ 257 nm ($\epsilon$ 17700).

NMR: $\sigma_{ppm}^{D_2O-K_2CO_3}$ 3.40 (1 H, d, 20 Hz, 2-H), 3.78 (1 H, d, 20 Hz, 2-H), 4.00 (1 H, d, 13 Hz, 3-CH$_2$), 4.35 (1 H, d, 13 Hz, 3-CH$_2$), 5.02 (1 H, d, 4 Hz, 6-H), 5.40 (1 H, d, 4 Hz, 7-H), 6.70 (1 H, d, 9 Hz, pyridazine-H), 7.40 (1 H, d, 9 Hz, pyridazine-H).

Anal. Calcd. for $C_{13}H_{12}N_6O_4S_2 \cdot H_2O$: C, 39.19; H, 3.54; N, 21.09; S, 16.09. Found: C, 39.40; H, 3.39; N, 20.36; S, 15.89.

7-Amino-3-(pyrido[2,1-c]-s-triazol-3-ylthiomethyl)-3-cephem-4-carboxylic acid (4f)

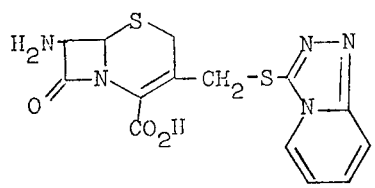

7-Amino-3-(s-triazolo[4,3-a]pyridin-3-ylthiomethyl-3-cephem-4-carboxylic acid (4f)

To a hot (60°) solution of 3-mercapto-s-triazolo[4,3-a]pyridine [D. S. Tarhell et al., J. Am. Chem. Soc. 70, 1381 (1948)] (1.51 g., 10 mmole) and NaHCO$_3$ (1.68 g., 20 mmole) in 0.1 M pH 7.4 phosphate buffer (50 ml.) was added portionwise 7-ACA (2.72 g., 10 mmole) and the mixture was heated at 80°–85° for 30 min. The reaction mixture being treated with carbon, the filtrate was acidified to pH 5 with dil. HCl to give 7-amino-3-(s-triazolo[4,3-a]pyridin-3-ylthiomethyl)-3-cephem-4-carboxylic acid which was collected by filtration, washed with water (10 ml.) and dried in vacuo on $P_2O_5$. Yield 1.40 g. (39%). M.p. 215°–220° (dec.).

IR: $\nu_{max}^{KBr}$ 1805, 1620, 1530, 1410, 1545 cm$^{-1}$.

UV: $\lambda_{max}^{1\%NaHCO_3}$ 280 nm ($\epsilon$ 13200).

NMR: $\delta_{ppm}^{D_2O+K_2CO_3}$ 3.25 (1 H, d, 18 Hz, 2-H), 3.63 (1H, d, 13 Hz, 3-H), 3.68 (1 H, d, 18 Hz, 2-H), 4.18 (1 H, d, 13 Hz, 3-H), 4.7-5.3 (2 H, m, 6-H & 7-H).

Anal. Calcd. for $C_{14}H_{13}N_5O_3S_2$: C, 46.27; H, 3.61; N, 19.27; S, 17.65. Found: C, 45.81; 45.74; H, 3.58, 3.69; N, 18.21, 18.13; S, 17.08.

7-Amino-3-pyridazino[2,1-c]-s-triazol-3-ylthiomethyl)-3-cephem-4-carboxylic acid (4g)

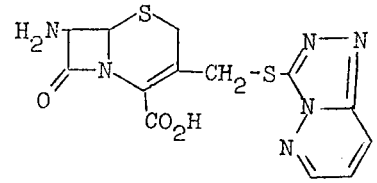

3-Mercapto-s-triazolo[4,3-b]pyridazine

A mixture of 1.20 g. (8 mmole) of 3-chloro-s-triazolo[4,3-b]pyridazine [P. Francavilla and F. Lauvia, J. Het. Chem., 8, 415 (1971) and 120 g. (16 mmole) of KSH in 20 ml. of ethanol was heated for 8 hours at 130° in a sealed tube. After cooling the mixture was evaporated to dryness and the residue was dissolved in 100 ml. of water, treated with active carbon, acidified to pH 1 with dil. HCl to precipitate 3-mercapto-s-triazolo[4,3-b]pyridazine which was collected, washed with 10 ml. of water and dried in vacuo over $P_2O_5$ to yield 0.75 g. (62%), m.p. 260°–270° (dec.).

IR: $\nu_{max}^{KBr}$ 3080, 2940, 2760, 1620, 1500, 1280, 1055 cm$^{-1}$.

NMR: $\sigma_{ppm}^{DMSO-d_6}$ 6.99 (1 H, d-d, 4 & 10 Hz, 7-H), 7.67 (1 H, d-d, 2 & 10 Hz, 8-H), 8.15 (1 H, d-d, 2 & 4 Hz, 6-H), 12.3 (1 H, br-s, disappear by addition of $D_2O$).

Anal. Calcd. for $C_5H_4N_4S \cdot 1/2H_2O$: C, 37.26; H, 3.13; N, 34.76. Found: C, 37.35; H, 2.32; N, 34.81.

7-Amino-3-(s-triazolo[4,3-b]pyridazin-3-ylthiomethyl)-3-cephem-4-carboxylic acid (4g)

7-ACA (1.36 g., 5 mmole) was added portionwise to a solution of 0.68 g. (4.5 mmole) of 3-mercapto-s-triazolo[4,3-b]pyridazine and 0.84 g. (10 mmole) of NaHCO$_3$ in 20 ml. of 0.1 M pH 7.4 phosphate buffer at 40°–50°. The mixture was heated at 80°–85° for 40 min., treated with a small amount of active carbon and acidified with dil. HCl to pH 4 to precipitate 7-amino-3-(s-triazolo[4,3-b]pyridazin-3-ylthiomethyl)-3-cephem-4-carboxylic acid which was collected, washed with 20 ml. of water and dried in vacuo on $P_2O_5$ to yield 0.81 g. (49%), M.p. > 300°.

IR: $\nu_{max}^{KBr}$ 1705, 1620, 1540, 1415, 1350 cm$^{-1}$.

UV: $\lambda_{max}^{1\%NaHCO_3}$ 275 nm ( 13100)

NMR: $\sigma_{ppm}^{D_2O+K_2CO_3}$ 3.35 (1 H, d, 18 Hz, 2-H), 3.86 (1 H, d, 18 Hz, 2-H), 4.80 (1 H, d-d, 4 & 2 Hz, 6-H), 5.24 (1 H, d, 4 Hz, 7-H), 7.1-8.6 (3 H, m, pyridazine-H).

Anal. Calcd. for $C_{13}H_{12}N_6O_3S_2 \cdot H_2O$: C, 40.83; H, 3.69; N, 21.96; S, 16.78. Found: C, 41.15; H, 3.24; N, 20.37; S, 17.90.

7-Amino-3-(1,2,3-triazol-5-ylthiomethyl)-3-cephem-4-carboxylic acid (4h)

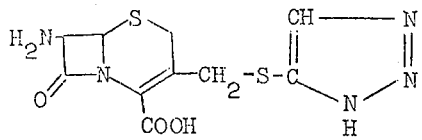

Synthesis of potassium 1,2,3-triazole-5-thiolate

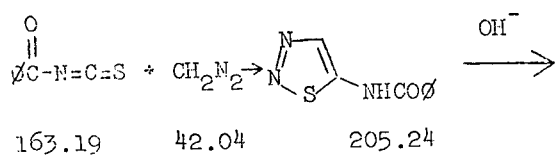

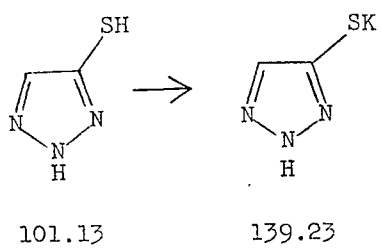

The synthesis of the thiol was accomplished by a procedure essentially identical to that described in the literature [J. Goerdler and G. Gnad, Chem. Ber. 99, 1618 (1966)].

5-Benzamido-1,2,3-thiadiazole

To a stirred solution of benzoylisothiocyanate (50.6 g., 310 mmoles) in commercial anhydrous ether (400 ml.), maintained at 0° and in a nitrogen atmosphere, was added dropwise with vigorous stirring, 0.685 N ethereal diazomethane (453 ml., 310 mmoles). When the addition was completed, the mixture was stirred for 1 hour at 0°, the solid was collected by filtration and dried in vacuo. The melting point of the crude material (23.3 g.) thus obtained was observed somewhere in the region 232° to 257°. Goerdler reported M.p. 267° for the pure material. A small second crop (2.1 g.) was obtained by evaporation of the mother liquor in vacuo. The total yield was therefore 40%.

1,2,3-Triazole-5-thiol

A solution of the above benzamido compound (8.2 g., 40 mmoles) in a 2 N sodium hydroxide (80 ml., 160 mmoles) was heated under reflux temperature in a nitrogen atmosphere for 24 hours. The solution was cooled to 0° in ice, and concentrated hydrochloric acid (26 ml.) was added, while a continuous stream of nitrogen was passed through the solution. The benzoic acid which precipitated was collected by filtration; the filtrate was saturated with sodium chloride and the additional benzoic acid which separated was removed by filtration. The filtration was immediately extracted with ethyl acetate, the extract was washed with saturated salt solution, dried over magnesium sulfate and then evaporated in vacuo. The viscous oil which remained was immediately evaporatively distilled in vacuo (70°–75°/0.001 mm.) to give an oil (2.84 g., 70%) which solidified (m.p. 52°–59°; Goerdler reported m.p. 60°) spontaneously.

Potassium 1,2,3-Triazole-5-thiolate

To a solution of the above thiol (2.84 g., 28.1 mmoles) in absolute ethanol (28 ml.) was added 1.93 N alcoholic potassium hydroxide solution (14.5 ml.). The solution was then diluted with anhydrous ether until crystallization of the salt was completed. The solid was collected by filtration, washed with ether, and dried in vacuo. The salt obtained in this manner (3.65 g., 93%) had m.p. 225° with decomposition.

7-Amino-3-[S-(1,2,3-triazole-5-yl)-thiomethyl]3-cephem-4-carboxylic acid (4h)

Ten grams (0.075 mole) of 5-mercapto-1,2,3-triazole potassium salt was added to a stirred slurry of 19 g. (0.07 mole) of purified 7-aminocephalosporanic acid and 5.9 g. (0.07 mole) of $NaHCO_3$ in 350 ml. of 0.1M phosphate buffer (pH 6.4) and the mixture heated and stirred at 55° C. for 3½ hours under a nitrogen atmosphere. The resulting solution was cooled to 22° C. and the pH adjusted to 5.5 with 40% $H_3PO_4$. The resulting precipitate was filtered off, washed with cold water (50 ml.) and air dried. The yield of 7-amino-3-[S-(1,2,3-triazole-5-yl)thiomethyl]-3-cephem-4-carboxylic acid was 8 g., dec. pt. 230° C. IR analysis showed some decomposition of the β-lactam ring but it was used "as is" for the next step.

Anal. Calcd. for $C_{10}H_{11}N_5O_3S_2$: C, 38.39; H, 3.54. Found: C, 38.36; H, 3.78.

Purification of 7-Amino-3-(1,2,3-triazol-5-ylthiomethyl)-3-cephem-4-carboxylic acid (4h)

Crude 7-amino-3-(1,2,3-triazol-5-ylthiomethyl)-3-cephem-4-carboxylic acid (16.1 g.) containing approximately 20 mole % of 7-aminocephalosporanic acid as an imputity, was brought into solution with 600 ml. of methanol and 40 ml. of conc. HCl. After carbon treatment, the solution was diluted with 1.5 l. of ice water and extracted once with ethyl acetate. The aqueous phase was concentrated at reduced pressure to remove methanol. The cold aqueous concentrate was then adjusted slowly to pH 4.0 with 20% sodium hydroxide causing the product to crystallize. The product was collected by filtration, washed with water and methanol and dried in vacuo over phosphorus pentoxide; 11.4 g. The NMR spectrum indicated that this product contained about 7 mole % of 7aminocephalosporanic acid as an impurity.

The above purification was repeated on 11.4 g. of the product using 425 ml. of methanol, 28 ml. of conc. HCl and 1 l. of ice water yielding 0.8 g. of product. The NMR spectrum was fully consistent for the desired product and indicated no trace of 7-aminocephalosporanic acid an an impurity.

Anal. Calcd. for $C_{10}H_{15}N_5O_3S_2$: C, 38.42; H, 3.55; N, 22.40. Found: C, 39.06; 38.53; H, 3.56, 3.51; N, 22.05, 21.60; $H_2O$, 1.78.

7-Amino-3-[2-(1,3,4-thiadiazolyl)-thiomethyl]-3-cephem-4-carboxylic acid (4i)

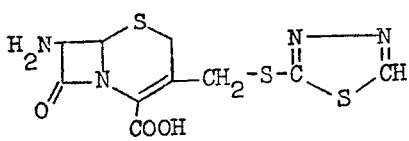

2-Mercapto-1,3,4-thiadiazole

The procedure of J. Goerdeler, J. Ohm and O. Tegtmeyer, Berichte 89, 1534 (1956) was followed. To a solution of 160 ml. of 48% hydrobromic acid and 100 mg. of powdered copper at −7° was added slowly with alternation 13.6 g. (0.1 mole) of 2-amino-1,3,4-thiadiazole (Eastman) and 32 g. of sodium nitrite in small portions over a period of one-half hour. The mixture was stirred for 1 ½ hours at 0° and for 1 hour at room temperature. The mixture was then neutralized with 50% potassium hydroxide to pH 9.5. The mixture was filtered and the filtrate was continuously extracted with ether for 6 hours. The ether was evaporated to 15 mm (25°) to a solid which was dissolved in 40 ml. of ethyl alcohol and treated with 5 g. of thiourea. The solution was heated at reflux for 1 ½ hours. A solution of 4.5 g. of potassium hydroxide in 65 ml. of water was added and the mixture was heated at reflux for an additional 1 ½ hours. The alcohol was evaporated at 15 mm. (32°) and the aqueous residue was neutralized with concentrated hydrochloric acid to pH 3.5. After cooling for 2 hours in an ice bath 3.5 g. of 2-mercapto-1,3,4-thiadiazole as yellow crystals were collected and weighed 3.5 g. M.p. 125°–127°. The IR and NMR spectra were consistent for the structure.

7-Amino-3-[2-(1,3,4-thiadiazolyl)-thiomethyl]-3-cephem-4-carboxylic acid (4i)

To a suspension of 8.1 g. (.03 mole) of 7-aminocephalosporanic acid and 3.5 g. (.03 mole) 2-mercapto-1,3,4-thiadiazole in 200 ml. of .1 M phosphate buffer (pH 6.5) was added with stirring 5.4 g. (.064 mole) of sodium bicarbonate. The mixture was stirred at 55° under nitrogen and all of the solid dissolved. The stirring was continued for 3 hours and the solution was cooled to 5° and adjusted to pH 5 with glacial acetic acid. The mixture was stored for 2 hours and the product, 7-amino-3-[2-(1,3,4-thiadiazolyl)-thiomethyl]-3-cephem-4-carboxylic acid, was collected and weighed 9 g., M.p. >140° (slow decomp.). The IR and NMR spectra were consistent for the structure.

7-Amino-3-[2-(5-hydroxymethyl-1,3,4-thiadiazolyl)-thiomethyl]-3-cephem-4-carboxylic acid (4j)

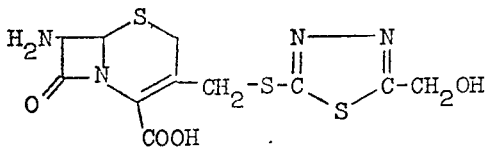

1-Hydroxyacetylthiosemicarbazide

A mixture of 18.2 g. (0.2 mole) of thiosemicarbazide and 30.4 g. (0.4 mole) of glycollic acid was heated together at 80°–90° for 2 hours with good stirring. The mixture was cooled at room temp. and washed with cold abs. alcohol. The solid was collected and air dried to weigh 40 g. The product was recrystallized from 100 ml. of boiling 50% alcohol to yield 23 g. of the crystalline 1-hydroxyacetylthiosemicarbazide. M.p. 189°–190°.

Anal. Calcd. for $C_3H_7N_3OS$, C, 24.18; H, 4.74; N, 28.21; S, 21.51. Found: C, 24.08; H, 4.50; N, 27.67; S, 21.35.

The IR and NMR spectra were consistent for the structure.

2-Acetoxymethyl-5-amino-1,3,4-thiadiazole

A mixture of 22.4 g. (0.15 mole) of 1-hydroxyacetylthiosemicarbazide and 60 ml. of acetyl chloride was stirred at room temperature for 2 hours and then heated to 40° until all the solid had dissolved (ca. 2 hours). The acetyl chloride was removed under reduced pressure 40° (15 min.) and the residue was stirred with 100 ml. of ice water. The mixture was adjusted to pH 9.2 with 10% KOH and the product was collected. The crude solid was recrystallized from absolute alcohol to yield after air drying 6 g. of crystalline 2-acetoxymethyl-5-amino-1,3,4-thiadiazole, M.p. 191°–192° C.

Anal. Calcd. for $C_5H_7N_3O_2S$: C, 34.63; H, 4.07; N, 24.26. Found: C, 35.16; H, 4.35; N, 24.38.

2-Hydroxymethyl-5-mercapto-1,3,4-thiadiazole

The procedure of Goerdler et al. was followed using 34.6 g. grams (0.2 mole) of 2-acetoxymethyl-5-amino-1,3,4-thiadiazole and 64 grams (0.9 mole) of sodium nitrite in 320 ml. of 48% hydrobromic acid and 0.1 gram of powdered copper. The bromo compound was treated with 7.6 grams (0.1 mole) of thiourea and 11.2 grams of potassium hydroxide in 25 ml. of water. Upon acidification with 6 N hydrochloric acid the mercaptan was extracted in ethyl acetate and treated with 17 grams of potassium 2-ethylhexanoate. The potassium salt was collected, washed with ethyl acetate and dried to weigh 12.2 grams. The salt was recrystallized from acetone-water to give 7.6 grams of crystalline potassium 2-hydroxymethyl-5-mercapto-1,3,4-thiadiazole, M.p. 130°–131° C.

Anal. Calcd. for $C_3H_3KN_2S_2O.H_2O$: C, 17.64; H, 2.46; N, 13.70. Found: C, 17.81; H, 2.43; N, 13.66

The IR and NMR spectra were consistent for the structure.

7-Amino-3-[2-(5-hydroxymethyl-1,3,4-thiadiazolyl)-thiomethyl]-3-cephem-4-carboxylic acid (4j)

The procedure followed was the same as the procedure for the unsubstituted thiadiazole using 2.25 g. (0.012 mole) of mercaptan, 3.3 g. (0.012 mole) of 7-aminocephalosporanic acid and 1 g. (0.012 mole) of sodium bicarbonate in 100 ml., 1 M phosphate buffer to yield 3.15 g. of tan, solid 7-amino-3-[2-(5-hydroxymethyl-1,3,4-thiadiazolyl)thiomethyl]-3-cephem-4-carboxylic acid, M.p. 170°–175° C. decomp. The IR and NMR spectra were consistent for the structure.

DESCRIPTION OF THE PREFERRED EMBODIMENTS

EXAMPLE 1

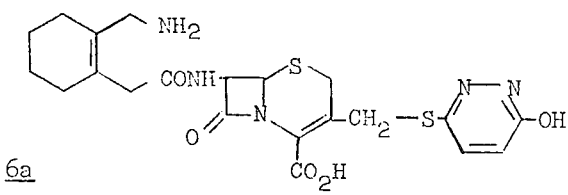

7-[α-(2-t-Butoxycarbonylaminomethyl-1-cyclohexenyl)acetamido]-3-(6-hydroxypryidazin-3-ylthiomethyl)-3-cephem-4-carboxylic acid (5a)

A mixture of 2 (1.08 g., 4 mmoles), 2,4-dinitrophenol (0.74 g., 4 mmoles) and DCC (0.82 g., 4 mmoles) in THF (20 ml.) was stirred for 1 hr. at room temperature and filtered to remove the precipitated dicyclohexylurea which was washed with THF (10 ml.). The combined filtrate and washings were cooled at 5° C. and poured in one portion into a cold solution of 7-amino-3-(6-hydroxypyridazin-3-ylthiomethyl)-3-cephem-4-carboxylic acid (1.02 g., 3 mmoles) and triethylamine (0.81 g., 8 mmoles) in 50% aqueous THF (20 ml.). The mixture was stirred overnight at room temperature and washed with ether (2 × 50 ml.). The aqueous layer was acidified to pH 2 with dil. HCl to precipitate crude 5a which was dissolved in THF (100 ml.) and filtered to remove insoluble material. The filtrate was treated with a small amount of carbon and dried over anhydrous sodium sulfate. Evaporation of the solvent under reduced pressure afforded 5a as an oily residue which was solidified by trituration in ether (100 ml.). Yield 0.84 g. (47%). M.p. 185°–195° C. (dec.).

IR: $\nu_{max}^{nuj}$ 3250, 1780, 1660, 1580, 1530, 1370, 1250, 1160 cm$^{-1}$.

NMR: $\delta_{ppm}^{DMSO-d_6}$ 1.40 (9H, s, t-Bu-H), 5.13 (1H, d, 4Hz, 6-H), 5.70 (1H, d-d, 4 and 8 Hz, 7-H), 6.88 (1H, d, 10 Hz, pyridazine-H), 7.45 (1H, d, 10 Hz, pyridazine-H), 9.0 (1H, d, 8 Hz, CONH), 13.2 (1H, br-s, —OH).

Anal. Calcd. for $C_{26}H_{33}N_5O_7S_2 \cdot 1/2 H_2O$: C, 51.98; H, 5.70; N, 11.65; S, 10.67. Found: C, 51.53; 51.56; H, 5.63, 5.80; N, 11.28, 11.34; S, 11.48, 11.31.

7-[α-(2-aminomethyl-1-cyclohexenyl)acetamido]-3-(6-hydroxypyridazin-3-ylthiomethyl)-3-cephem-4-carboxylic acid (6a)

To trifluoroacetic acid (1.5 ml.) was added 5a (0.80 g., 1.4 mmoles) and the mixture was stirred for 30 min. at room temperature and diluted with ether (50 ml.) to precipitate the trifluoroacetate of 6a which was collected by filtration and slurried in water (2 ml.). The mixture was adjusted at pH 6 with ammonium hydroxide and diluted with acetonitrile (200 ml.) to precipitate 6a. Yield 0.64 g. (93%). M.p. 200–208 (dec.).

IR: $\nu_{max}^{nuj}$ 1780, 1680 - 1640, 1580 cm$^{-1}$.

UV: $\lambda_{max}^{1\%K_2CO_3}$ 255 nm (ε, 14100).

Anal. Calcd. for $C_{21}H_{25}N_5O_5S_2 \cdot 3\frac{1}{2} H_2O$: C, 45.48; H, 5.82; N, 12.63; S, 11.56. Found: C, 45.73, 45.83; H, 4.50, 4.47; N, 12.45, 12.59; S, 11.83, 12.06.

EXAMPLE 2

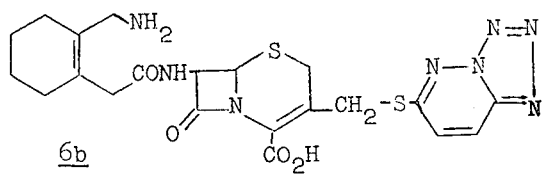

7-[α-(2-t-Butoxycarbonylaminomethyl-1-cyclohexenyl)acetamido]-3-(pyridazino[2,3-d]tetrazol-6-ylthiomethyl)-3-cephem-4-carboxylic acid (5b)

A mixture of 2 (1.08 g., 4 mmoles), 2,4-dinitrophenol (0.74 g., 4 mmoles) and DCC (0.82 g., 4 mmoles) in THF (20 ml.) was stirred for 1 hr. at room temperature and filtered to remove the dicyclohexylurea which was washed with THF (10 ml.). The combined filtrate and washing were cooled at 5° C. and poured into a solution of 7-amino-3-(pyridazino[2,3-d]tetrazol-6-ylthiomethyl)-3-cephem-4-carboxylic acid (4b) (1.08 g., 3 mmoles) and triethylamine (0.81 g., 8 mmoles) in 50% aqueous THF (20 ml.) at 5° C. The mixture was stirred overnight at room temperature and washed with ether (2 × 50 ml.). The aqueous layer was acidified to pH 2 with dil. HCl and extracted with ethyl acetate (3 × 50 ml.). The combined extracts were washed with water (50 ml.), treated with carbon and dried over anhydrous $Na_2SO_4$. Removal of the solvent under reduced pressure gave 5b as an oil which was solidified by trituration with ether (50 ml.). The product was collected by filtration, washed with ether and dried. Yield 0.94 g. (51%). M.p. 125°–134°C. (dec.).

IR: $\nu_{max}^{KBr}$ 1780, 1680, 1520, 1370, 1250, 1160 cm$^{-1}$.

NMR: $\delta_{ppm}^{DMSO-d_6}$ 1.40 (9H, s, t-Bu-H), 4.23 (1H, d, 14 Hz, 3-CH$_2$S), 4.70 (1H, d, 15 Hz, 3-CH$_2$S), 5.15 (1H, d, 4 Hz, 6-H), 5.78 (1H, d-d, 4 and 8 Hz, 7-H), 7.88 (1H, d, 10 Hz, pyridazine-H), 8.75 (1H, d, 10 Hz, pyridazine-H), 9.0 (1H, d, 8 Hz, 7-CONH).

Anal. Calcd. for $C_{26}H_{32}N_8O_6S_2$: C, 50.64; H, 5.23; S, 10.40. Found: C, 50.36, 50.42; H, 5.11, 5.21; S, 9.60.

7-[α-(2-aminomethyl-1-cyclohexenyl)acetamido]-3-(pyradazino[2,3-d]tetrazol-6-ylthiomethyl)-3-cephem-4-carboxylic acid (6b)

To trifluoroacetic acid (1.5 ml.) was added 5b (0.90 g., 1.5 mmoles) at 0° C. and the mixture was stirred for 30 min. at room temperature. The mixture was diluted with ether (50 ml.) to precipitate the trifluoroacetate which was collected by filtration and suspended in water (2 ml.). The suspension was adjusted at pH 6 with ammonium hydroxide and diluted with acetonitrile (200 ml.) to precipitate 6b which was collected by filtration and dried. Yield 0.65 g. (83%). M.p. 184°–188° C. (dec.).

IR: $\nu_{max}^{nuj}$ 1780, 1620, 1570 cm$^{-1}$.

UV: $\lambda_{max}^{1\%K_2CO_3}$ 245 nm (ε, 18500), 255 nm (sh) (ε, 16300), 275 nm (sh) (ε, 10700), 315 nm (sh) (ε, 4700).

Anal. Calcd. for $c_{21}H_{24}N_8O_4S_2 \cdot \frac{1}{2}H_2O$: C, 47.99; H, 4.79; N, 21.32; S, 12.20. Found: C, 48.21, 47.90; H, 4.61, 4.67; N, 20.68, 20.63; S, 11.47.

EXAMPLE 3

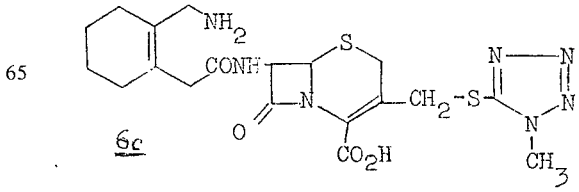

7-{2-[(N-t-Butoxycarbonylamino)methyl-1-cyclohexen-1-yl]acetamido}-3-(1-methyltetrazol-5-ylthiomethyl)-3-cephem-4-carboxylic acid (5c)

A mixture of 2 (1.30 g., 4.8 mmoles), 2,4-dinitrophenol (0.88 g., 4.8 mmoles) and DCC (0.99 g., 4.8 mmoles) in THF (20 ml.) was stirred for 1 hr. at room temperature to precipitate the dicyclohexylurea which was removed by filtration and the bed was washed with THF (5 ml.). The combined filtrate and washings were poured into a cold solution of 7-amino-3-(1-methyltetrazol-5-ylthiomethyl)-3-cephem-4-carboxylic acid (4c) (1.31 g., 4 mmoles) and triethylamine (1.01 g., 10 mmoles) in 50% aqueous THF with stirring at 5° C. The mixture was stirred overnight at room temperature, evaporated under reduced pressure below 40° C. and washed well with ether (3 × 30 ml.). The aqueous layer was acidified to pH 2 with dil. HCl and extracted with ethyl acetate (4 × 50 ml.). The combined extracts were treated with a small amount of carbon and dried. Removal of the solvent below 40° C. under reduced pressure afforded an oily residue which was solidified by trituration with ether (100 ml.) to give 1.33 g. of the product 5c. M.p. 146°–159° C. (dec.).

IR: $\nu_{max}^{nuj}$ 1780, 1700 (sh), 1680, 1520, 1240, 1155 cm$^{-1}$.

NMR: $\delta_{ppm}^{DMSO-d_6}$ 1.42 (9H, s, t-butyl-$\underline{H}$), 1.5 – 1.7 (4H, m, aliphatic methylene-$\underline{H}$), 1.8 – 3.3 (4H, m, allylic methylene-$\underline{H}$), 4.12 (3H, s, N-CH$_3$), 5.15 (1H, d, 5 Hz, 6-$\underline{H}$), 5.80 (1H, d-d 5 and 8 Hz, 7-$\underline{H}$), 6.85 (1H, br-s, NHBOC), 9.00 (1H, d, 8 Hz, CONH).

Anal. Calcd. for C$_{24}$H$_{33}$N$_7$O$_6$S$_2$: C, 49.73; H, 5.74; N, 16.91; S, 11.06. Found: C, 49.46, 49.46; H, 5.53, 5.62; N, 16.00, 15.97; S, 11.01.

7-[(2-aminomethyl-1-cyclohexen-1-yl)acetamido]-3-(1-methyltetrazol-5-ylthiomethyl)-3-cephem-4-carboxylic acid (6c)

A mixture of trifluoroacetic acid (2 ml.) and 5c (1.30 g., 2.4 mmoles) was stirred magnetically for 30 min. at room temperature. The mixture was diluted with ether (50 ml.) to precipitate the trifluoroacetate of 6c. The trifluoroacetate was suspended in a small amount of water (2 ml.) and the suspension was adjusted at pH 6 with ammonium hydroxide and diluted with acetonitrile (200 ml.) to give 6c which was washed with acetonitrile (50 ml.) and dried.

M.p. 194°–207° C. (dec.). Yield 0.80 g. (69%).

IR: $\nu_{max}^{nuj}$ 1770, 1630, 1590, 1370 cm$^{-1}$.

UV: $\lambda_{max}^{1\%K_2CO_3}$ 270 nm ($\epsilon$, 10000).

Anal. Calcd. for C$_{19}$H$_{25}$N$_7$O$_4$S$_2$·H$_2$O: C, 45.86; H, 5.47; N, 19.70; S, 12.89. Found: C, 45.89, 46.18; H, 5.26, 5.28; N, 19.74, 19.82; S, 12.49.

7-[α-(2-t-Butoxycarbonylaminomethyl-1-cyclohexenyl)acetamido]-3-(5-methyl-1,3,4-thiadiazol-2-ylthiomethyl)-3-cephem-4-carboxylic acid (5d)

A mixture of 2 (1.08 g., 4 mmoles), 2,4-dinitrophenol (0.74 g., 4 mmoles) and DCC (0.82 g., 4 mmoles) in THF (20 ml.) was stirred for 1 hr. at room temperature and filtered to remove the dicyclohexylurea which was washed with THF (10 ml.). The combined filtrate and washings were cooled at 5° C. and poured in one portion into a cold (5° C.) solution of 7-amino-3-(5-methyl-1,3,4-thiadiazol-2-ylthiomethyl)-3-cephem-4-carboxylic acid (4d) (0.94 g., 3 mmoles) and triethylamine (0.81 g., 8 mmoles) in 50% aqueous THF (20 ml.). The reaction mixture was stirred overnight at room temperature and washed with ether (2 × 50 ml.). The aqueous layer was acidified to pH 2 with dil. HCl and extracted with ethyl acetate (3 × 50 ml.). The combined extracts were washed with water (50 ml.), treated with a small amount of carbon, dried with Na$_2$SO$_4$ and evaporated under reduced pressure to give an oily residue which was solidified by trituration with ether - n-hexane (1:1, 100 ml.). The product 5d was collected by filtration, washed with n-hexane (50 ml.) and dried. Yield 1.29 g. (72%). M.p. 95°–102° C. (dec.).

IR: $\nu_{max}^{nuj}$ 1780, 1680, 1520, 1245, 1160 cm$^{-1}$.

NMR: $\delta_{ppm}^{DMSO-d_6}$ 1.30 (9H, s, t-Bu-$\underline{H}$), 2.58 (3H, s, CH$_3$), 4.03 (1H, d, 14 Hz, 3-CH$_2$S), 4.38 (1H, d, 14 Hz, 3-CH$_2$S), 4.88 (1H, d, 4 Hz, 6-$\underline{H}$), 5.46 (1H, d-d, 4 and 8 Hz, 7-$\underline{H}$), 8.54 (1H, d, 8 Hz, CONH).

Anal. Calcd. for C$_{25}$H$_{33}$N$_5$O$_6$S$_3$: C, 50.40; H, 5.58; N, 11.76. Found: C, 50.76, 50.98; H, 5.67, 5.67; N, 11.27, 11.28.

7-[α-(2-aminomethyl-1-cyclohexenyl)acetamido]-3-(5-methyl-1,3,4-thiadiazol-2-ylthiomethyl)-3-cephem-4-carboxylic acid (6d)

A mixture of trifluoroacetic acid (2 ml.) and 5d (1.20 g., 2 mmoles) was stirred for 30 min at room temperature and diluted with ether (50 ml.) to precipitate the trifluoroacetate of 6d. The trifluoroacetate was slurried in water (2 ml.), adjusted at pH 6 with ammonium hydroxide and diluted with acetonitrile (200 ml.) to precipitate 6d. Yield 0.75 g. (76%). M.p. 215° – 220° C. (dec.).

IR: $\nu_{max}^{nuj}$ 1760, 1640, 1580 cm$^{-1}$.

UV: $\lambda_{max}^{1\%K_2CO_3}$ 276 nm ($\epsilon$, 13400).

Anal. Calcd. for C$_{20}$H$_{25}$N$_5$O$_4$S$_3$·½H$_2$O: C, 47.60; H, 5.19; N, 13.87; S, 19.06. Found: C, 47.14, 47.23; H, 4.96, 5.07; N, 13.61, 13.70; S, 18.66.

EXAMPLE 4

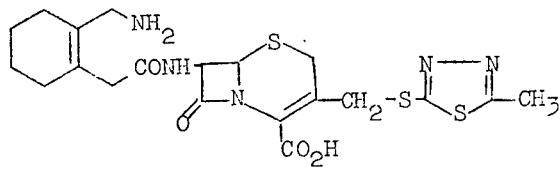

6d

EXAMPLE 5

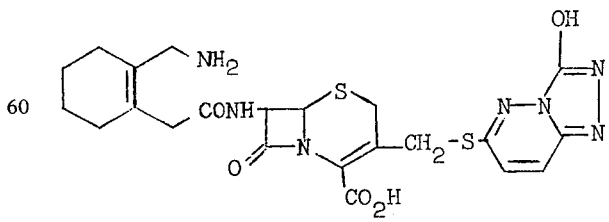

6e

7-[α-(2-t-Butoxycarbonylaminomethyl-1-cyclohexenyl)acetamido]-3-(3-hydroxypyridazino-[3.2-c]-s-triazol-6-ylthiomethyl)-3-cephem-4-carboxylic acid (5e)

A mixture of 2 (1.08 g., 4 mmoles), 2,4-dinitrophenol (0.74 g., 4 mmoles) and DCC (0.82 g., 4 mmoles) in THF (20 ml.) was stirred for 1 hr. at room temperature and filtered to remove the precipitated dicyclohexylurea which was washed with THF (10 ml.). The combined filtrate and washings were cooled at 5° C. and poured in one portion into a cold (5° C.) solution of 7-amino-3-(3-hydroxypyridazino[3,2-c]-s-triazol-6-ylthiomethyl)-3-cephem-4-carboxylic acid (1.14 g., 3 mmoles) and triethylamine (0.81 g., 8 mmoles) in 50% aqueous THF (20 ml.). The mixture was stirred overnight at room temperature and washed with ether (2 × 50 ml.). The aqueous layer was acidified to pH 2 with dil. HCl. The precipitate was dissolved at 50° C. in THF (100 ml.), treated with a small amount of carbon and dried with anhydrous $Na_2SO_4$. Evaporation of the solvent under reduced pressure afforded an oily residue which was solidified by trituration with ether (50 ml. to give 5e. Yield 0.85 g. (45%). M.p. 190°–198° C. (dec.).

IR: $\nu_{max}^{KBr}$ 1780, 1700, 1520, 1350, 1250, 1160 $cm^{-1}$.

NMR: $\delta_{ppm}^{DMSO-d_6}$ 1.40 (9H, s, t-Bu-$\underline{H}$), 5.20 (1H, d, 4 Hz, 6-$\underline{H}$), 5.80 (1H, m, 7-$\underline{H}$), 7.10 (1H, d, 10 Hz, pyridazin-$\underline{H}$), 7.80 (1H, d, 10 Hz, pyridazin-$\underline{H}$).

Anal. Calcd. for $C_{27}H_{33}N_7O_7S_2 \cdot \frac{1}{2}H_2O$: C, 50.61; H, 5.35; S, 10.01. Found: C, 50.59, 50.68; H, 5.40, 5.59; S, 9.57, 9.55.

7-[α-(2-Aminomethyl-1-cyclohexenyl)acetamido]-3-(3-hydroxypyridazino-[3,2-c]-3-triazol-6-ylthiomethyl)-3-cephem-4-carboxylic acid (6e)

A mixture of trifluoroacetic acid (2 ml.) and 5e (0.81 g., 1.3 mmoles) was stirred for 30 min. at room temperature and diluted with ether (50 ml.) to precipitate the trifluoroacetate of 6e. The trifluoroacetate was slurried in water (2 ml.). The mixture was adjusted at pH 6 with ammonium hydroxide and diluted with acetonitrile (200 ml.) to give 6e. Yield 0.57 g. (82%). M.p. 225°–234° C. (dec.).

IR: $\nu_{max}^{nuj}$ 1770, 1710, 1630, 1545, $cm^{-1}$.

IV: $\lambda_{max}^{1\%K_2CO_3}$ 260 nm ($\epsilon$, 18100), 305 nm (sh) ($\epsilon$, 6300).

Anal. Calcd. for $C_{22}H_{25}N_7O_5S_2 \cdot 3H_2O$: C, 45.12; H, 5.34; N, 16.74; S, 10.94. Found: C, 45.28, 45.44; H, 4.35, 4.45; N, 16.56, 16.66; S, 11.75.

EXAMPLE 6

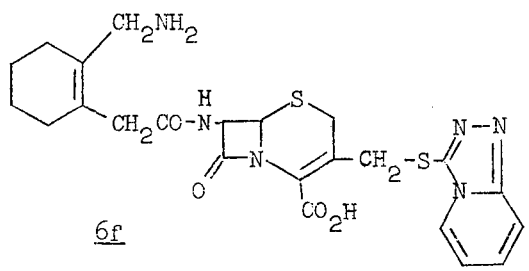

6f

7-[(2-N-t-Butoxycarbonylaminomethyl-1-cyclohexenyl)acetamido]-3-(pyrido[2,1-c]-s-triazol-3-ylthiomethyl)-3-cephem-4-carboxylic acid (5f)

DCC (740 mg., 3.6 mmoles) is added to a solution of 950 mg. (3.3 mmoles) of α-[2-(t-butoxycarbonylaminomethyl)-1-cyclohexenyl]acetic acid (2), and 660 mg. (3.6 mmoles) of 2,4-dinitrophenol in 30 ml. of THF and the mixture is stirred for one hour at room temperature and the urea filtered off. To the filtrate is added a solution of 1.1 g. (3 mmoles) of 7-amino-3-(pyrido[2,1-c]-s-triazol-3-ylthiomethyl)-3-ylthiomethyl)-3-cephem-4-carboxylic acid (4f) and 1.25 ml. (9 mmoles) of triethylamine in 30 ml. of water and the mixture is stirred for 18 hours at room temperature. The THF is removed under reduced pressure below 40° C. and the residue is washed with ether (2 × 10 ml.), acidified with 6 N HCl and extracted with ethyl acetate (5 × 10 ml.). The combined extracts are washed with water (2 × 10 ml.) and a saturated NaCl solution (10 ml.) and evaporated to dryness below 40° C. Trituration of the residue with ether gives about 1.2 g. of solid 5f.

7-[(2-Aminomethyl-1-cyclohexenyl)acetamido]-3-(pyrido[2,1-c]-s-triazol-3-ylthiomethyl)-3-cephem-4-carboxylic acid (6f)

Trifluoroacetic acid (2.5 ml.) is added to the BOC-blocked cephalosporin 5f (1.1 g., 1.8 mmoles) with stirring for 1.5 hours under cooling and the mixture is diluted with 100 ml. of ether to separate the trifluoroacetate of 6f which is dissolved in 5 ml. of water, adjusted to pH 6 with conc. $NH_4OH$ and diluted with 100 ml. of acetonitrile. The resulting yellow precipitate is collected by filtration and washed with acetonitrile to give about 700 mg. (76%) of solid 6f.

EXAMPLE 7

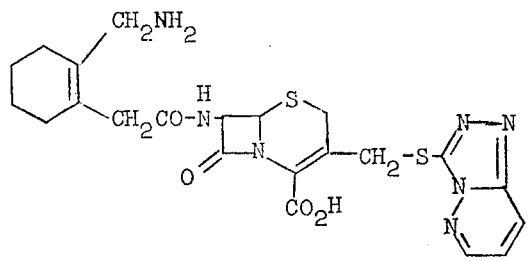

7-[(2-N-t-Butoxycarbonylaminomethyl-1-cyclohexenyl)acetamido]-3-pyridazino[2,1-c]-s-triazol-3-ylthiomethyl)-3-cephem-4-carboxylic acid (5g)

To a solution of α-[2-(t-butoxycarbonylaminomethyl)-1-cyclohexenyl]acetic acid (2) (1.07 g., 4 mmoles) and 2,4-dinitrophenol (0.74 g., 4 mmoles) in dry THF (10 ml.) is added DCC (0.82 g., 4 mmoles) and the mixture is stirred for one hour at room temperature to precipitate the urea which is removed by filtration. To the filtrate is added in one portion a cold solution of 7-amino-3-pyridazino[2,1-c]-s-triazol-3-ylthiomethyl)-3-cephem-4-carboxylic acid (4g) (1.09 g., 3 mmoles) and triethylamine (0.81 g., 8 mmoles) in 50% aqueous THF (20 ml.) and the mixture is stirred for 20 hours at room temperature. The reaction mixture is washed with ether (2 × 50 ml.), acidified to pH 2 with diluted hydrochloric acid and extracted with ethyl acetate (6 × 50 ml.). The combined extracts are washed with water (2 × 30 ml.), treated with carbon and dried on anhydrous sodium sulfate. Evaporation of the solvent under reduced pressure affords an oily residue which is solidified by trituration with ether (50 ml.) to give about 0.6 g. of solid 5g.

7-(2-Aminomethyl-1-cyclohexenylacetamido)-3-(pyridazino[2,1-c]-s-triazol-3-ylthiomethyl)-3-cephem-4-carboxylic acid (6g)

A mixture of 5g (0.53 g., 0.86 mmole) in trifluoroacetic acid (1 ml.) is stirred for one hour at 0° – 5° C. and diluted with ether (30 ml.) to precipitate the trifluoroacetate of 6g which is collected by filtration and dissolved in water (4 ml.). The solution is adjusted to pH 6 with ammonium hydroxide and diluted with acetonitrile (100 ml.) to precipitate 6g which is collected by filtration, washed with acetonitrile (30 ml.) and dried in vacuo over $P_2O_5$ to yield about 0.3 g. solid 6g.

EXAMPLE 8

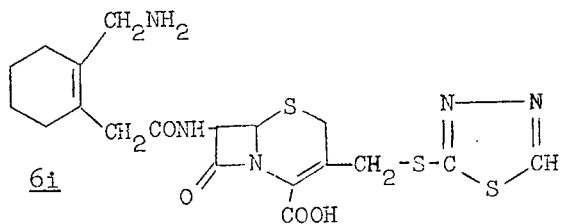

6i

7-[(2-tert.-Butoxycarbonylaminomethyl-1-cyclohexenyl)acetamido]-3-(1,3,4-thiadiazole-2-mercaptomethyl)-3-cephem-4-carboxylic acid (5i)

To a stirred solution of 1.10 g. (0.0041 mole) of 2 and 0.80 g. (0.0044 mole) of 2,4-dinitrophenol in 40 ml. of ethyl acetate is added in one portion 0.90 g. (0.0044 mole) of N,N'-dicyclohexylcarbodiimide and the mixture is stirred for 3 hr. at 25°. The dicyclohexylurea is collected and the filtrate is evaporated at 45° (15 mm) to give the activated ester as an oil. The oil is dissolved in 30 ml. of THF. A solution of 1.22 g. (0.0037 mole) of 7-amino-3-(1,3,4-thiadiazole-2-mercaptomethyl)-3-cephem-4-carboxylic acid and 1.03 ml. (0.0074 mole) of triethylamine in 20 ml. of 50% THF-water is added to the solution of the activated ester and stirred for 18 hr. at 25°. The THF is removed at 40° (15 mm.) and the concentrate (10 ml.) is washed with ether ( 5 × 100 ml.) and acidified to pH 2 with 40% phosphoric acid. The mixture is extracted with ethyl acetate (6 × 100 ml.) and the combined extracts are washed with water and finally with a saturated sodium chloride solution. The ethyl acetate solution is evaporated at 40° (15 mm.) to a volume of 20 ml. and diluted with 30 ml. of Skellysolve B to precipitate the solid product 5i which is collected and dried for 16 hr. in vacuo over $P_2O_5$ at 25° to yield about 1.4 g.

7-[(2-Aminomethyl-1-cyclohexenyl)acetamido]-3-(1,3,4-thiadiazole-2-mercaptomethyl)-3-cephem-4-carboxylic acid (6i)

A solution of 1.30 g. (0.00226 mole) of (5i) and 3.0 ml. trifluoroacetic acid is stirred for 1 hr. at 0°. The solution is diluted with 200 ml. of ether and the precipitate collected by filtration. The trifluoroacetate salt is suspended in 40 ml. of water and adjusted to pH 6.0 with dilute ammonium hydroxide. The gummy residue is then triturated with 25 ml. of acetonitrile to give about 350 mg. of 6i as a white powder. The product is dried for 16 hr. in vacuo over $P_2O_5$ at 25°.

EXAMPLE 9

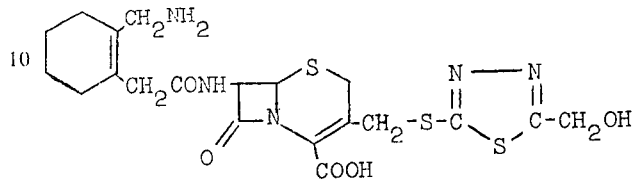

7-[(2-Aminomethyl-1-cyclohexenyl)acetamido]-3-(5-hydroxymethyl-1,3,4-thiadiazole-2-mercaptomethyl)-3-cephem-4-carboxylic acid (6j)

The procedure is the same as that of Example 8, except that the product 6j is collected from the water to obtain about 340 mg. as a tan powder. A second fraction is obtained from the filtrate to give about 200 mg. of 6j as a yellow crystalline solid.

EXAMPLE 10

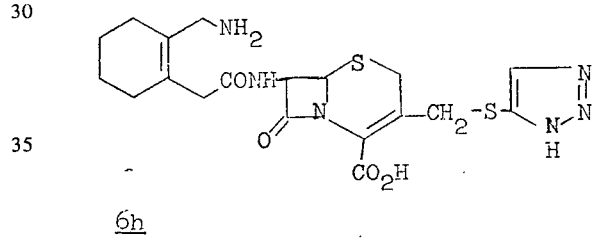

6h

7-[α-(2-t-Butoxycarbonylaminomethyl-1-cyclohexenyl)acetamido]-3-(1H-1,2,3-triazol-4-ylthiomethyl)-3-cephem-4-carboxylic acid (5h)

A mixture of 2 (1.08 g., 4 mmoles), 2,4-dinitrophenol (0.74 g., 4 mmoles) and DCC (0.82 g., 4 mmoles) in THF (20 ml.) was stirred for 1 hr. at room temperature and filtered to remove the dicyclohexylurea which was washed with THF (10 ml.). The combined filtrate and washings were poured in one portion at 5° C. into a solution of 7-amino-3-(1H-1,2,3-triazol-4-ylthiomethyl)-3-cephem-4-carboxylic acid (4h) (1.24 g., 4 mmoles) and triethylamine (0.81 g., 8 mmoles) in 50% aqueous THF (20 ml.). The reaction mixture was stirred overnight at room temperature and washed with ether (2 × 50 ml.). The aqueous layer was acidified to pH 2 with dil. HCl and extracted with ethyl acetate (3 × 50 ml.). The combined extracts were washed with water (50 ml.), treated with a small amount of carbon and dried over anhydrous $Na_2SO_4$. Removal of the solvent under reduced pressure afforded an oily residue which solidified by trituration with ether - n-hexane (1:1, 100 ml.) to give 0.60 g. (26%) of 5h. M.p. 120°–128° C. (dec.).

IR: $\nu_{max}^{nuj}$ 1780, 1720, 1680, 1520, 1250, 1160 cm$^{-1}$.

NMR: $\delta_{ppm}^{DMSO-d_6}$ 1.38 (9H, s, t-Bu-H), 5.08 (1H, d, 4 Hz, 6-H), 5.65 (1H, d-d, 4 and 8 Hz, 7-H), 8.00 (1H, s, triazol-H), 8.92 (1H, d, 8 Hz CONH).

Anal. Calcd. for $C_{24}H_{32}N_6O_6S_2 \cdot 1/2H_2O$: C, 50.25; H, 5.80; N, 14.65; S, 11.18. Found: C, 50.51, 50.69; H, 5.73, 5.65; N, 14.57, 14.25; S, 10.05, 10.16.

7-[α-(2-Aminomethyl-1-cyclohexenyl)acetamido]-3-(1H-1,2,3-triazol-4-ylthiomethyl)-3-cephem-4-carboxylic acid (6h)

A mixture of trifluoroacetic acid (1 ml.) and 5h (0.55 g., 0.98 mmoles) was stirred for 30 min. at room temperature and diluted with ether (50 ml.) to give the precipitate which was collected by filtration and slurried in a small amount of water (2 ml.). The mixture was adjusted to pH 6 with ammonium hydroxide and diluted with acetonitrile (200 ml.) to precipitate 6h which was washed with acetonitrile (50 ml.). Yield 0.36 g. (80%). M.p. 203° – 215° C. (dec.).

IR: $\nu_{max}^{nuj}$ 1760, 1630, 1570 cm$^{-1}$

UV: $\lambda_{max}^{1\%K_2CO_3}$ 266 nm (ε, 8000).

Anal. Calcd. for $C_{19}H_{24}N_6O_4S_2 \cdot 1\ 1/2\ H_2O$: C, 46.42; H, 5.54; N, 17.10; S, 13.04. Found: C, 46.06, 46.16; H, 5.18, 5.28; N, 18.06, 18.02; S, 12.37.

EXAMPLE 11

The salicylaldehyde adduct of 7-[(2-aminomethyl-1-cyclohexenyl)acetamido]-3-(3-hydroxypyridazino[3,2-c]-s-triazol-6-ylthiomethyl)-3-cephem-4-carboxylic acid (7c)

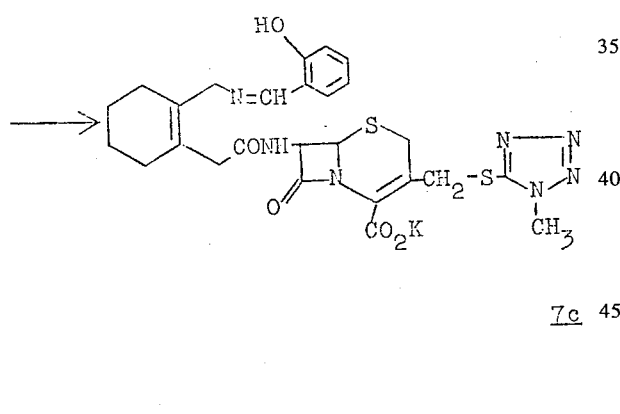

To a stirred suspension of 6c (Example 3, 766 mg., 1.6 mmoles) and triethylamine (300 mg., 3 mmoles) in methanol (8 ml.) is added salicylaldehyde (370 mg., 3 mmoles) and the mixture is stirred for 30 min. at room temperature to make a clear dark yellow solution. The solution is treated with a small amount of carbon and KEH (2 ml., 1 M solution in ethyl acetate of potassium 2-ethylhexanoate) is added to the filtrate. The mixture is diluted with a large amount of ether (100 ml.) to precipitate the solid product 7c which is collected by filtration, washed with ether (30 ml.) and dried. Yield about 750 mgm.

EXAMPLE 12

The salicylaldehyde adduct of 7-[(2-aminomethyl-1-cyclohexenyl)acetamido]-3-(5-methyl-1,3,4-thiadiazol-2-ylthiomethyl)-3-cephem-4-carboxylic acid (7d)

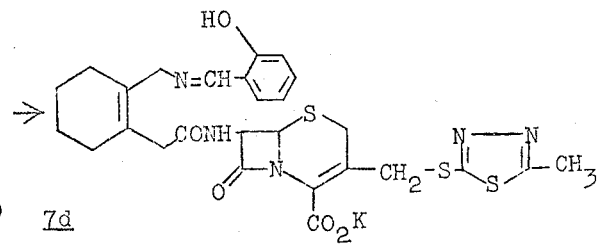

To a stirred mixture of 6d (Example 4, 778 mg., 1.6 mmoles) and triethylamine (300 mg., 3 mmoles) is added salicylaldehyde (370 mg., 3 mmoles) and the suspension is stirred for 15 min. at room temperature to make a clear dark yellow solution which is treated with a small amount of carbon. KEH (2 ml., 1 M solution in ethyl acetate) is added to the filtrate. The mixture is diluted with a large amount of ether (100 ml.) to precipitate the product 7d which is collected by filtration, washed with ether (30 ml.) and dried. Yield about 850 mg.

EXAMPLE 13

The salicylaldehyde adduct of 7-[(2-aminomethyl-1-cyclohexenyl)acetamido]-3-(3-hydroxypyridazino[3,2-c]-s-triazol-6-ylthiomethyl)-3-cephem-4-carboxylic acid (7e)

To a stirred suspension of 6e (Example 5, 754 mg., 1.42 mmoles) and triethylamine (300 mg., 3 mmoles) in N,N-dimethylformamide (7ml.) is added salicylaldehyde (370 mg., 3 mmoles) and the suspension is stirred for 1.5 hr. at room temperature to be a clear dark yellow solution which is treated with a small amount of carbon. KFH (1.5 ml., 1 M solution in ethyl acetate) is added to the filtrate. The mixture is diluted with a large amount of ether (100 ml.) to precipitate the product 7e which is washed with ether (30 ml.) and dried. Yield about 900 mg.

EXAMPLE 14

The potassium salt of the compound of Example 3 is prepared by adding a solution of potassium 2-ethylhexanoate (KEH) in ethyl acetate to a solution of the cephalosporin (zwitterion) (6c) in DMSO to precipitate the desired potassium salt.

EXAMPLE 15

The sodium salt of the compound of Example 3 is prepared by pre-formation of its diethylammonium salt in methanol followed by addition of a solution of sodium 2-ethylhexanoate (SEH) in ethyl acetate and then dilution with isopropanol to precipitate the desired sodium salt which has a solubility in water greater than 250 mgm./ml.

EXAMPLE 16

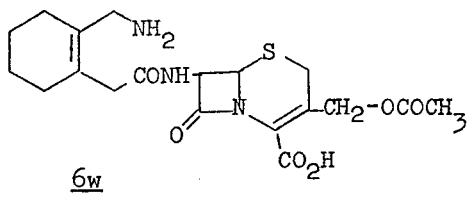

6w

7-[α-(2-t-Butoxycarbonylaminomethyl-1-cyclohexenylacetamido]cephalosporanic acid (5w)

A mixture of 2 (1.08 g., 4 mmoles), 2,4-dinitrophenol (0.74 g., 4 mmoles) and DCC (0.82 g., 4 mmoles) in THF (20 ml.) was stirred for 1 hr. at room temperature and filtered to remove the dicyclohexylurea which was washed with THF (10 ml.). The combined filtrate and washings were poured in one portion at 5° C. into a solution of 7-ACA (4w) (0.82 g., 3 mmoles) and triethylamine (0.81 g., 8 mmoles) in 50% aqueous THF (20 ml.). The reaction mixture was stirred overnight at room temperature and washed with ether (2 × 50 ml.). The aqueous layer was acidified to pH 2 with dil. HCl and extracted with ethyl acetate (3 × 50 ml.). The combined extracts were washed with water (50 ml.) and dried over anhydrous $Na_2SO_4$. Evaporation of the solvent under reduced pressure afforded 5w as an oily residue which was solidified by trituration with ether-n-hexane (1:1, 100 ml.) and washed with n-hexane (50 ml.). Yield 1.24 g. (79%). M.p. 100°–110° C.

IR: $\nu_{max}^{nuj}$ 1780, 1730 - 1640, 1520, 1355, 1225 $cm^{-1}$.

NMR: $\delta_{ppm}^{DMSO-d_6}$ 1.23 (9H, s, t-Bu-$\underline{H}$), 1.96 (3H, s, 3-OAc), 4.48 (1H, d, 13 Hz, 3-$CH_2$), 4.83 (1H, d, 13 Hz, 3-$CH_2$), 4.89 (1H, d, 4 Hz, 6-$\underline{H}$), 5.48 (1H, d-d, 4 and 8 Hz, 7-$\underline{H}$), 8.5 (1H, d, 8Hz, CONH).

Anal. Calcd. for $C_{24}H_{33}N_3O_8S.½ H_2O$: C, 54.12; H, 6.43; N, 7.88; S, 6.02. Found: C, 54.16, 54.07; H, 6.19, 6.22; N, 8.36, 8.34; S, 5.61, 5.79.

7-[α-(2-Aminomethy-1-cyclohexenyl)acetamido]-cephalosporanic acid (6w)

A mixture of trifluoroacetic acid (2 ml.) and 5w (1.20 g., 2.3 mmoles) was stirred for 30 min. at room temperature and diluted with ether (50 ml.) to precipitate the trifluoroacetate which was slurried in water (2 ml.). The mixture was adjusted to pH 6 with ammonium hydroxide and diluted with acetonitrile (200 ml.) to precipitate 6w. Yield 0.68 g. (69%). M.p. 250° – 260° C. (dec.).

IR: $\nu_{max}^{nuj}$ 1800, 1735, 1625, 1570, 1230 $cm^{-1}$.
UV: $\lambda_{max}^{1\%K_2CO_3}$ 255 nm ($\epsilon$, 7100).

Anal. Calcd. for $C_{19}H_{25}N_3O_6S.½ H_2O$: C, 52.76; H, 6.05; N, 9.71; S, 7.41. Found: C, 52.36, 52.15; H, 6.09, 6.06; N, 9.74, 9.71; S, 7.71, 7.81.

The solubility was 5.4 (BA) and 5.3 (UV).

EXAMPLE 17

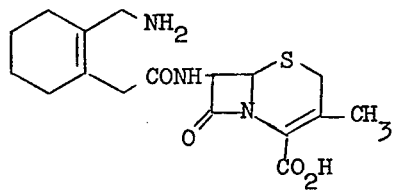

6x

7-[α-(2-t-Butoxycarbonylaminomethyl-1-cyclohexenyl)acetamido]desacetoxy-cephalosporanic acid (5x)

A mixture of 2 (1.08 g., 4 mmoles), 2.4-dinitrophenol (0.74 g., 4 mmoles) and DCC (0.82 g., 4 mmoles) in THF (20 ml.) was stirred for 1 hr. at room temperature and filtered to remove the precipitated dicyclohexylurea which was washed with THF (10 ml.). The combined filtrate and washings were poured in one portion at 5° C. into a solution of 7-ACDA (4x) (0.64 g., 3 mmoles) and triethylamine (0.81 g., 8 mmoles) in 50% aqueous THF (20 ml.). The reaction mixture was stirred at room temperature for 18 hr. and washed with ether (2 × 50 ml.). The aqueous layer was acidified to pH 2 with dil. HCl and extracted with ethyl acetate (2 × 50 ml.). The combined extracts were washed with water (50 ml.), treated with a small amount of carbon and dried over anhydrous $Na_2SO_4$. Evaporation of the solvent under reduced pressure afforded an oily residue which was solidified by trituration in ether-n-hexane (1:1, 100 ml.) to give 5x. Yield 0.88 g. (63%). M.p. 120° – 127° (dec.).

IR: $\nu_{max}^{nuj}$ 1780, 1680, 1520, 1250, 1160 $cm^{-1}$.

NRM: $\delta_{ppm}^{DMSO-d_6}$ 1.35 (9H, s, t-Bu-$\underline{H}$), 1.98 (3H, s, 3-$CH_3$), 4.86 (1H, d, 4 Hz, 6-$\underline{H}$), 5.40 (1H, d-d, 4 and 8 Hz, 7-$\underline{H}$), 8.50 (1H, d, 8 Hz, CONH).

Anal. Calcd. for $C_{22}H_{31}N_3O_6S$: C, 56.76; H, 6.71; N, 9.03; S, 6.89. Found: C, 56.21, 56.21; H, 6.65, 6.77; N, 8.98, 9.04; S, 6.71; 7.00.

7-[α-(2-Aminomethyl-1-cyclohexenyl)acetamido]-desacetoxycephalosporanic acid (6x)

To a cooled (0° C.) trifluoroacetic acid (2 ml.) was added 5x (0.84 g., 1.8 mmoles) and the mixture was stirred for one-half hr. at room temperature. The mixture was diluted with ether (50 ml.) to precipitate the trifluoroacetate which was slurried in water (2 ml.). The mixture was adjusted at pH 6 with ammonium hydroxide and diluted with acetonitrile (200 ml.) to give 6x which was washed with acetonitrile (20 ml.). Yield 0.48 g. (73%). M.p. 240°–245° C. (dec.).

IR: $\nu_{max}^{nuj}$ 3580, 3300, 1750, 1640, 1525 $cm^{-1}$.
UV: $\lambda_{max}^{1\%K_2CO_3}$ 260 nm ($\epsilon$, 6500).

Anal. Calcd. for $C_{17}H_{23}N_3O_4S.H_2O$: C, 53.24; H, 6.57; N, 10.95; S, 8.36. Found: C, 53.83, 53.87; H, 6.06, 6.23; N, 11.08, 10.99 S, 8.75, 9.01.

The solubility was 4.1 (BA) and 3.3 (UV).

The corresponding compounds containing a 3-acetoxymethyl group and a 3-methyl group were prepared and compared in vitro with the compound of Example 3 with the following results

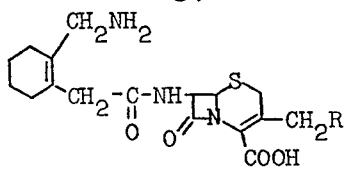

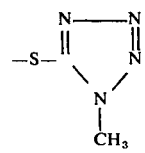

M.I.C. (Mcg./ml.)

| Organism | | R=<br>—OCOCH₃<br>6w | —H<br>6x | 6c |
|---|---|---|---|---|
| S. aureus Smith⁺ | A9537 | 0.8 | > 3.1, 25 | 0.2–0.4 |
| S. aureus Smith⁺<br>+ 50% serum | A9537 | 3.1 | > 6.3, 25 | 0.8–1.6 |
| S. aureus Russel | | 0.8–1.6 | >12.5, 12.5 | 0.4–0.8 |
| S. aureus BX1633 | A9606 | 3.1 | >12.5, 25 | 1.6 |
| Str. pyogenes<br>+ 5% serum | A9604 | 0.8–0.16 | 1.25–2.5 | 0.04–0.08 |
| D. pneumoniae<br>+ 5% serum | A9585 | 0.16–0.31 | > 2.5, 10 | 0.04–0.08 |
| Mycobacterium 607 | | > 100 | >100 | >100 |
| E. coli NIHJ | | 25–50 | >100 | 1.6–3.1 |
| E. coli ATCC 8739 | | 25 | >100 | 3.1–6.3 |
| E. coli Juhl⁺ | A15119 | 25 | >100 | 3.1– 6.3 |
| K. pneumoniae⁺ | A9977 | 12.5–25 | >100 | 0.8–3.1 |
| K. pneumoniae⁺ | A15130 | 12.5–50 | >100 | 3.1–6.3 |
| Pr. mirabilis⁺ | A9900 | 50 | >100 | 100 |
| Pr. morganii⁺ | A15153 | > 100 | >100 | >100 |
| Sal. enteritidis⁺ | A9531 | 12.5 | >100 | 1.6–3.1 |
| Ser. marcescens⁺ | A20019 | > 100 | >100 | >100 |
| Ps. aeruginosa⁺ | A9843 | > 100 | >100 | >100 |

*50% Nutrient Broth - 45% Antibiotic Assay Broth
⁺at 10⁻⁴ dilution.

The above samples after solution in Nutrient Broth were found to exhibit the indicated Minimum Inhibitory Concentrations (M.I.C.) in meg./ml. versus the indicated microorganisms as determined by overnight incubation at 37° C. by Tube Dilution The excellent in vivo activity of the preferred compound of the present invention (6c, BB-S336) was demonstrated by comparing it with results previously obtained by substantially the same procedure for MR-S94 in determinations (by subcutaneous administration of the drug to infected mice) of the minimum curative dose for 50% of the mice ($CD_{50}$) in mgm./kg. versus lethal doses of the indicated microorganisms with the following results:

| Challenge<br>Organism | $CD_{50}$ in mgm./kg. | |
|---|---|---|
| | BB-S336 | MR-S94 |
| S. aureus BX-1633 | 2.4 | 3.4 |
| E coli Juhl | 5.4 | 4.4 |

Determination of Solubilities

Solubilities of cephalosporin derivatives in 0.1 M pH 7.0 phosphate buffer are determined by bioassay and also by spectroscopic method (when the sample shows UV absorption) each with its own standard which has been completely solubilized. The test solution and the standard solution are prepared as described below.

Preparation of the test solution

About 10 mg. (1) of a sample is placed in a vial and mixed with 1 ml. of 0.1 M phosphate buffer (pH 7.0). The vial is stoppered, sealed with a metal cap, placed on a rotary shaker and agitated at 160 rpm for 4 hr. at 25° C. The solution is filtered through a Millipore filter (HAWP 01300, mean pore size 0.45 μm). The filtrate is diluted to use for bioassay and UV assay as follows:

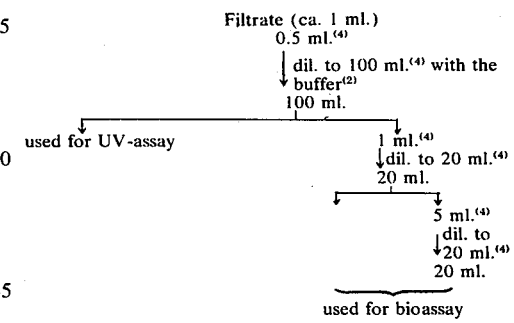

Preparation of the standard solution

About 2 mg. of the same sample is weighed precisely and dissolved in 4 ml. of 1% $K_2CO_3$ solution[3] (usually within one minute). The solution is diluted exactly to 50 ml. in a flask with 0.1 M pH 7.0 phosphate buffer and used for the preparation of the standard solutions for bioassay and UV-assay as follows:

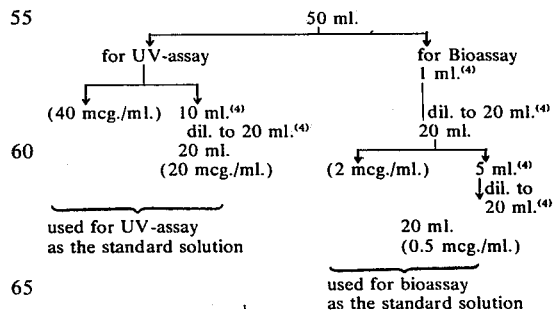

(1) A 20 mg. or more sample is used when the sample is expected to be more soluble.

(2) 0.1 M pH 7.0 phosphate buffer is used as a diluent in the present test and also as a reference solution in UV-assay.

(3) It was previously confirmed that almost the same result is obtained when the sample is solubilized in DMSO (dimethylsulfoxide) and then diluted similarily with the buffer.

(4) Volume of the solution is measured precisely with an appropriate pipette or flask.

Solubilities (mg./ml.) in 0.1 M phosphate buffer (pH 7.0)

| 7-sidechain R—NH—; R = | benzyl-CH₂NH₂/CO— | | cyclohexenyl-CH₂NH₂/CO— | |
|---|---|---|---|---|
| 3-sidechain —CH₂—S—R'; R'= | | | | |
| tetrazolyl | MR-S94 | | BB-S336 | (6c) |
| | BA | UV | BA | UV |
| | 2.0 | 1.9 | 25.6 | 24.6 |
| | | | 23.0 | 26.0 |
| 1,3-dimethyltetrazolyl (CH₃, CH₃) | MR-S96 | | BB-S341 | (6d) |
| | 1.2 | 0.9 | 4.3 | 4.6 |
| pyridazinyl-OH | BB-S150 | | BB-S340 | (6a) |
| | 4.4 | 4.4 | 16.8 | 16.0 |
| triazolopyridazinyl | BB-S226 | | BB-S338 | (6b) |
| | | 2.5 | 3.0 | 3.0 |
| | | 2.1 | | |
| | 3.8 | 3.5 | | |
| | | 2.2 | | |
| OH-triazolopyridazinyl | BB-S207 | | BB-S339 | (6e) |
| | BA | UV | BA | UV |
| | 4.2 | 3.9 | 8.0 | 8.1 |
| | | 3.6 | | |

BA: Bioassay, UV: UV-assay Results given for the same compound on different lines were obtained using samples from different lots.

We claim:
1. An acid having the formula

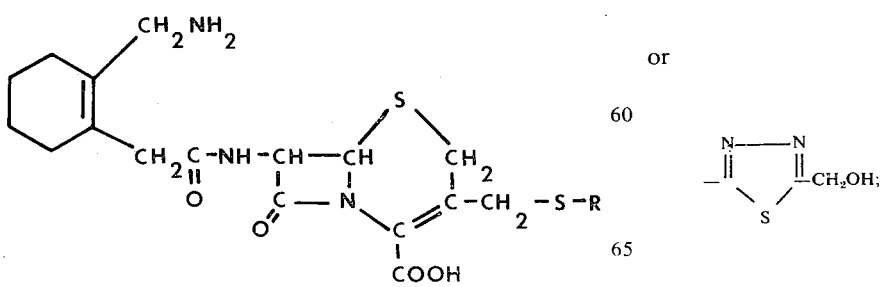

wherein R is

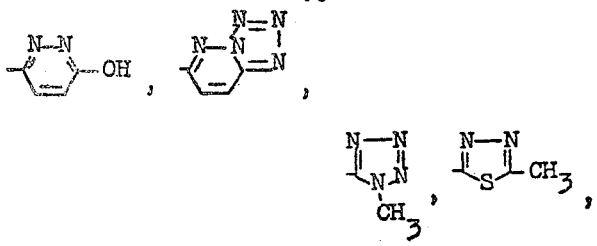

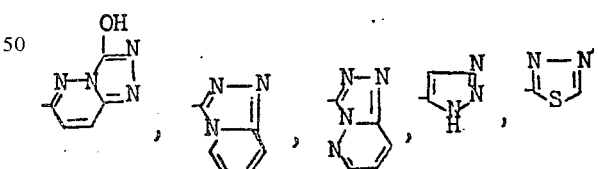

or

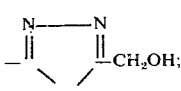

or a nontoxic, pharmaceutically acceptable salt thereof.

2. The acid of claim 1 having the formula

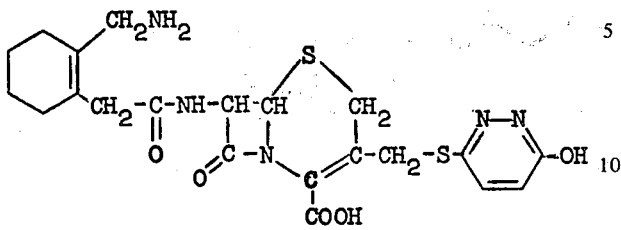

3. The sodium salt of the acid of claim 2.
4. The potassium salt of the acid of claim 2.
5. The zwitterion form of the acid of claim 2.
6. A nontoxic, pharmaceutically acceptable salt of the acid of claim 2.
7. The acid of claim 1 having the formula

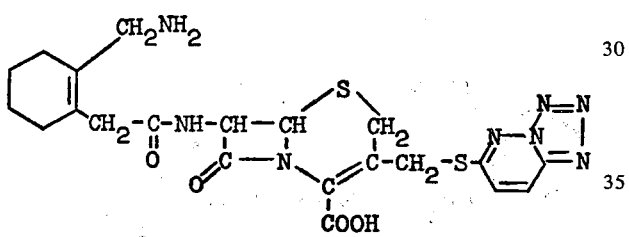

8. The sodium salt of the acid of claim 7.
9. The potassium salt of the acid of claim 7.
10. The zwitterion form of the acid of claim 7.
11. A nontoxic, pharmaceutically acceptable salt of the acid of claim 7.
12. The acid of claim 1 having the formula

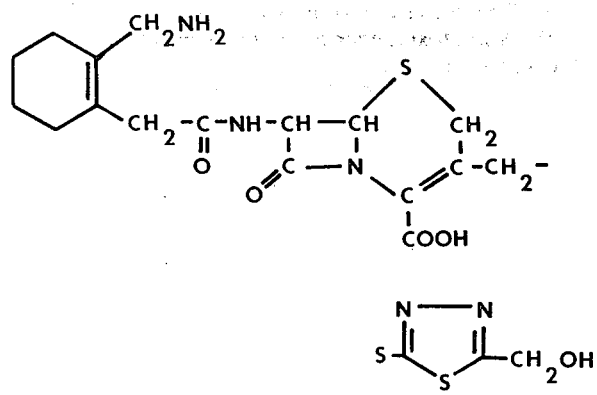

13. The sodium salt of the acid of claim 12.
14. The potassium salt of the acid of claim 12.
15. The zwitterion form of the acid of claim 12.

16. A nontoxic, pharmaceutically acceptable salt of the acid of claim 12.
17. The acid of claim 1 having the formula

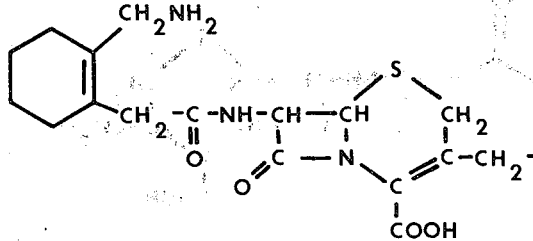

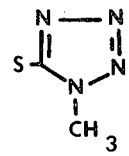

18. The sodium salt of the acid of claim 17.
19. The potassium salt of the acid of claim 17.
20. The zwitterion form of the acid of claim 17.
21. A nontoxic, pharmaceutically acceptable salt of the acid of claim 17.
22. The acid of claim 1 having the formula

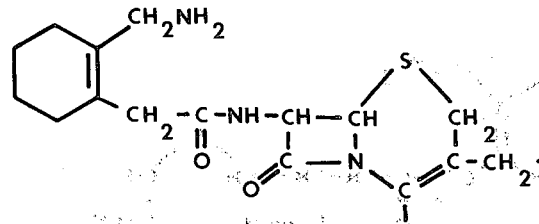

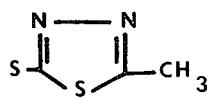

23. The sodium salt of the acid of claim 22.
24. The potassium salt of the acid of claim 22.
25. The zwitterion form of the acid of claim 22.
26. A nontoxic, pharmaceutically acceptable salt of the acid of claim 22.
27. The acid of claim 1 having the formula

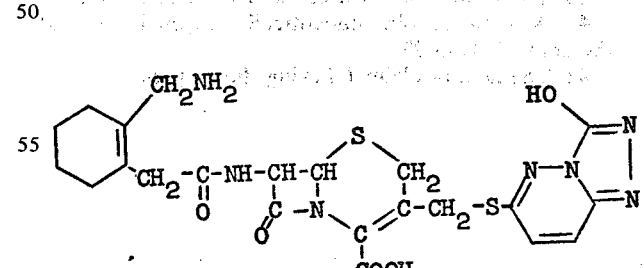

28. The sodium salt of the acid of claim 27.
29. The potassium salt of the acid of claim 27.
30. The zwitterion form of the acid of claim 27.
31. A nontoxic, pharmaceutically acceptable salt of the acid of claim 27.
32. The acid of claim 1 having the formula

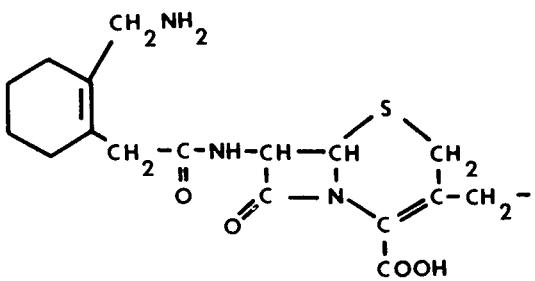

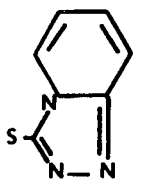

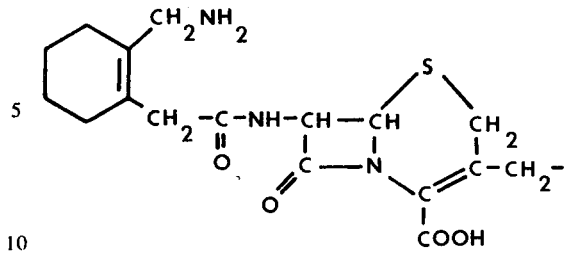

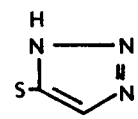

33. The sodium salt of the acid of claim 32.
34. The potassium salt of the acid of claim 32.
35. The zwitterion form of the acid of claim 32.
36. A nontoxic, pharmaceutically acceptable salt of the acid of claim 32.
37. The acid of claim 1 having the formula

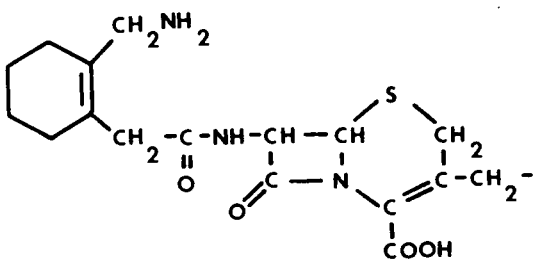

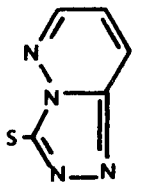

38. The sodium salt of the acid of claim 37.
39. The potassium salt of the acid of claim 37.
40. The zwitterion form of the acid of claim 37.
41. A nontoxic, pharmaceutically acceptable salt of the acid of claim 37.
42. The acid of claim 1 having the formula 43. The sodium salt of the acid of claim 42.
44. The potassium salt of the acid of claim 42.
45. The zwitterion form of the acid of claim 42.
46. A nontoxic, pharmaceutically acceptable salt of the acid of claim 42.
47. The acid of claim 1 having the formula 48. The sodium salt of the acid of claim 47.
49. The potassium salt of the acid of claim 47.
50. The zwitterion form of the acid of claim 47.
51. A nontoxic, pharmaceutically acceptable salt of the acid of claim 47.

* * * * *